US012673048B2

(12) United States Patent
Martinell Pedemonte et al.

(10) Patent No.: US 12,673,048 B2
(45) Date of Patent: Jul. 7, 2026

(54) METHOD OF ADMINISTERING A THERAPEUTICALLY EFFECTIVE AMOUNT OF 5-[[4-[2-[5-(1-HYDROXYETHYL) PYRIDIN-2-YL]ETHOXY]PHENYL] METHYL]-1,3-THIAZOLIDINE-2,4-DIONE

(71) Applicant: MINORYX THERAPEUTICS S.L., Mataró Barcelona (ES)

(72) Inventors: Marc Martinell Pedemonte, Mataró Barcelona (ES); Maria Pilar Pizcueta Lalanza, Mataró Barcelona (ES); Guillem Pina Laguna, Mataró Barcelona (ES); Uwe Meya, Mataró Barcelona (ES); Alan Bye, Horsham (GB)

(73) Assignee: MINORYX THERAPEUTICS S.L., Mataró Barcelona (ES)

( * ) Notice: Subject to any disclaimer, the term of this patent is extended or adjusted under 35 U.S.C. 154(b) by 317 days.

(21) Appl. No.: 16/972,368

(22) PCT Filed: Jun. 6, 2019

(86) PCT No.: PCT/IB2019/054743
§ 371 (c)(1),
(2) Date: Dec. 4, 2020

(87) PCT Pub. No.: WO2019/234689
PCT Pub. Date: Dec. 12, 2019

(65) Prior Publication Data

US 2021/0308113 A1 Oct. 7, 2021

(30) Foreign Application Priority Data

Jun. 6, 2018 (EP) .................................... 18382398

(51) Int. Cl.
*A61K 31/4439* (2006.01)
*A61K 9/00* (2006.01)

(52) U.S. Cl.
CPC ........ *A61K 31/4439* (2013.01); *A61K 9/0053* (2013.01)

(58) Field of Classification Search
CPC ........ A61K 31/4439; A61K 9/08; A61K 9/16; A61K 9/20; A61K 9/48; A61K 45/06; A61K 9/0053; A61P 1/16; A61P 25/00; A61P 25/28; C07D 417/12; Y02A 50/30
See application file for complete search history.

(56) References Cited

U.S. PATENT DOCUMENTS

2009/0171697 A1 * 7/2009 Glauser ................ C12Q 1/6883 705/3
2014/0114676 A1 * 4/2014 Holmes .................. G01N 33/94 705/2

FOREIGN PATENT DOCUMENTS

WO WO-2013040419 A1 3/2013
WO WO-2015150476 A1 * 10/2015 ......... A61K 31/4439
WO WO-2018100557 A1 6/2018
WO WO-2018116281 A1 6/2018
WO WO-2019234664 A1 12/2019
WO WO-2019234690 A1 12/2019
WO WO-2021220250 A1 11/2021

OTHER PUBLICATIONS

Kawaguchi-Suzuki et al. (J. Chromatogr. B 969 (2014) 219-223).*
Kawaguchi-Suzuki et al. (Aliment Pharmacol Ther. 2017;46:56-61).*
Kawaguchi-Suzuki et al. (J. Chromatogr. B 969 (2014) 219-223) (Year: 2014).*
Kawaguchi-Suzuki et al. (Aliment Pharmacol Ther. 2017;46:56-61) (Year: 2017).*
Sarafidis et al. (American Journal of Hypertension, 2006; 19(6): 646-653 (Year: 2006).*
Mosure et al., (2019), J Med Chem. Feb. 28, 2019;62(4):2008-2023. doi: 10.1021/acs.jmedchem.8b01573 (Year: 2019).*
Li et al., Clin. Exp. Obstet. Gynecol. 2014, 41(5), 499-506 (Year: 2014).*
International Search Report and Written Opinion for International Application No. PCT/IB2019/054743, European Patent Office, Netherlands, mailed on Sep. 23, 2019, 9 pages.
Kawaguchi-Suzuki, M., et al., "Pharmacodynamic Association Of Pioglitazone And Its Active Metabolites With Liver Outcomes Among Patients Diagnosed With Nonalcoholic Steatohepatitis," Clinical Pharmacology and Therapeutics 95(Suppl 1):S47, Abstract #PI-090, 1 page, Nature Publishing Group, United Kingdom (Feb. 2014).
Kawaguchi-Suzuki, M., et al., "Concentration-Dependent Response to Pioglitazone in Nonalcoholic Steatohepatitis," Alimentary Pharmacology & Therapeutics 46(1):56-61, John Wiley & Sons Ltd., (May 2017).
Almeida, S. et al., "Truncated areas under the curve in the assessment of pioglitazone bioequivalence" *Arzneimittelforschung* 61(1):32-39, Editio Cantor Verlag, Aulendorf (Germany), (2011).
Kawaguchi-Suzuki, M. et al., "A validated liquid chromatography tandem mass spectrometry method for simultaneous determination of pioglitazone, hydroxypioglitazone, and ketopioglitazone in human plasma and its application to a clinical study," *Journal of Chromatography B* 969:219-223, Elsevier B.V., (2014).

(Continued)

*Primary Examiner* — James H Alstrum-Acevedo
*Assistant Examiner* — Chantal Adlam
(74) *Attorney, Agent, or Firm* — STERNE, KESSLER, GOLDSTEIN & FOX P.L.L.C.

(57) ABSTRACT

The present disclosure provides methods of treating a disease or disorder in a patient comprising administering 5-[[4-[2-[5-(1-hydroxyethyl)pyridin-2-yl]ethoxy]phenyl]methyl]-1,3-thiazolidine-2,4-dione ("Compound (1)"), or a pharmaceutically acceptable salt thereof, to the patient, wherein the patient achieves a threshold steady-state plasma concentration of Compound (1). The present disclosure also provides methods of administering a therapeutically effective amount of Compound (1), or a pharmaceutically acceptable salt thereof, to a patient. Compound (1) is a PPAR-γ agonist that is used to treat a variety of diseases and disorders including, but not limited to, nonalcoholic steatohepatitis and central nervous system diseases, e.g., X-linked adrenoleukodystrophy, Friedreich's Ataxia.

12 Claims, 7 Drawing Sheets

(56) References Cited

OTHER PUBLICATIONS

Islambulchilar et al., “Rapid HPLC Determination of Pioglitazone in Human Plasma by Protein Precipitation and Its Application to Pharmacokinetic Studies,” Journal of AOAC International, 93(3): 876-881, AOAC International, (2010).
Fernandez, R.F., et al., “Peroxisome Proliferator-activated Receptor (PPAR) γ Agonism Facilitates Timely Resolution of Acute Sterile Inflammation in Chronic Granulomatous Disease (CGD),” J. Allergy Clin. Immunol. 125(2):AB56, Elsevier, Netherlands (Feb. 2010).
Lu, X., et al., “Expression and significance of peroxisome proliferator—activated receptor γ in pituitary adenomas”, Chin J. Neuromed. 5(12):1223-1225, Chinese Medical Journals Publishing House Co. Ltd, China (2006).
Peng, J., et al., “Peroxisome proliferator-activated receptor and inflammation as well as immune reaction,” Chemistry of Life 25(3):232-235, BMJ Publishing, United Kingdom (2005).
Runjian, R., et al., “Research progress of peroxisome proliferator-activated receptor gamma in inflammatory-related diseases,” Laboratory Medicine 32(3):153-157, Oxford University Press, United Kingdom (Feb. 2017).
Wang, L., et al., “PPAR-γ and thyroid disease,” Medical Recapitulate 16(2):164-166, Medical Review Editorial Department, China (2010).
Wang, Y., et al., “Progress in research on peroxisome proliferator-activated receptor-gamma and insulin resistance in polycystic ovary syndrome,” Journal of Foreign Medical Sciences (Section of Maternal and Child Health) 15(3):185-187, Ivyspring International Publisher, Australia (2004).
Zhang, W., et al., “Peroxisome Proliferators Activated Receptor Gamma: Structure Feather and Biological Function”, Chinese Journal of Animal Nutrition 24(9):1628-1635, Chinese Society of Animal Husbandry and Veterinary Medicine, China (2012).

* cited by examiner

Hela

METHOD OF ADMINISTERING A THERAPEUTICALLY EFFECTIVE AMOUNT OF 5-[[4-[2-[5-(1-HYDROXYETHYL) PYRIDIN-2-YL]ETHOXY]PHENYL] METHYL]-1,3-THIAZOLIDINE-2,4-DIONE

CROSS-REFERENCE TO RELATED APPLICATION

This application claims priority to European Application No. EP18382398.8, filed on Jun. 6, 2018, the entirety of which is incorporated by reference herein.

FIELD OF DISCLOSURE

The present disclosure provides methods of treating a disease or disorder in a patient comprising administering 5-[[4-[2-[5-(1-hydroxyethyl)pyridin-2-yl]ethoxy]phenyl] methyl]-1,3-thiazolidine-2,4-dione, or a pharmaceutically acceptable salt thereof, to the patient, wherein the patient achieves a threshold steady-state plasma concentration of 5-[[4-[2-[5-(1-hydroxyethyl)pyridin-2-yl]ethoxy]phenyl] methyl]-1,3-thiazolidine-2,4-dione. The present disclosure also provides methods of administering a therapeutically effective amount of 5-[[4-[2-[5-(1-hydroxyethyl)pyridin-2-yl]ethoxy]phenyl]methyl]-1,3-thiazolidine-2,4-dione, or a pharmaceutically acceptable salt thereof, to a patient. 5-[[4-[2-[5-(1-hydroxyethyl)pyridin-2-yl]ethoxy]phenyl]methyl]-1,3-thiazolidine-2,4-dione can be used to treat a variety of diseases and disorders including, but not limited to, nonalcoholic steatohepatitis (NASH) and central nervous system diseases, e.g., X-linked adrenoleukodystrophy (X-ALD), Friedreich's Ataxia.

BACKGROUND OF THE INVENTION

5-[[4-[2-[5-(1-hydroxyethyl)pyridin-2-yl]ethoxy]phenyl] methyl]-1,3-thiazolidine-2,4-dione (referred to herein as "Compound (1)") is a metabolite of pioglitazone see, e.g., Sohda et al., *Chem. Pharm. Bull.* 43(12):2168-2172 (1995); Maeshiba et al., *Arzneim.-Forsch/Drug Res.* 47(1):29-35 (1997) having selective peroxisome proliferator-activated receptor gamma (PPAR-γ) agonist activity. WO 2015/150476 A1 discloses Compound (1), and the pharmaceutically acceptable salts thereof, for use in the treatment of central nervous system diseases. International Appl. No. PCT/TB2017/057587 discloses Compound (1), and the pharmaceutically acceptable salts thereof, for the treatment of nonalcoholic fatty liver disease ("NAFLD"), nonalcoholic steatohepatitis ("NASH"), and other diseases and disorders.

BRIEF SUMMARY OF THE INVENTION

Compound (1), and pharmaceutically acceptable salts thereof, is orally bioavailable and displays linear pharmacokinetics in humans. But Applicant has found that large variations in drug clearance and plasma concentration among individual patients makes it unexpectedly difficult to administer a therapeutically effective amount of Compound (1) to patients using conventional dosing techniques. Because of this pharmacokinetic variability, there exists a need for improved methods of administering Compound (1), or a pharmaceutically acceptable salt thereof, to patients in need thereof, especially over extended periods of time, e.g., weeks, months, or years, to treat various diseases including X-ALD, Friedreich's Ataxia, and NASH.

In one aspect, the present disclosure provides a method of treating a disease or disorder in a patient in need thereof, the method comprising administering Compound (1), or a pharmaceutically acceptable salt thereof, to the patient, wherein:

(i) the steady-state area under the curve ($AUC_{ss}$) of Compound (1) in plasma from the patient is about 34 μg h/mL to about 300 μg h/mL;

(ii) the minimum steady-state plasma drug concentration ($C_{min\ ss}$) of Compound (1) in plasma from the patient is about 55 ng/mL to about 9126 ng/mL; or (iii) the $AUC_{ss}$ of Compound (1) in plasma from the patient is about 34 μg h/mL to about 300 μg h/mL, and the $C_{min\ ss}$ of Compound (1) in plasma from the patient is about 55 ng/mL to about 9126 ng/mL; and the $AUC_{ss}$ of (i), the $C_{min\ ss}$ of (ii), or the $AUC_{ss}$ and $C_{min\ ss}$ of (iii) is measured after at least five days of orally administering Compound (1), or a pharmaceutically acceptable salt thereof, to the patient per day.

In another aspect, the present disclosure provides a concentration control approach to administer a therapeutically effective amount of Compound (1), or a pharmaceutically acceptable salt thereof, to a patient in need thereof. This approach is based on the measured steady-state exposure, e.g., $AUC_{ss}$ or $C_{min\ ss}$, of Compound (1) in plasma. Using this approach, a calculated adjustment of the initial, e.g., the first 5-14 days, dosage amount of Compound (1), or pharmaceutically acceptable salt thereof, balances the therapeutic efficacy of Compound (1) against toxicity and unwanted side effects to provide the maximum benefit to patients over time, e.g., weeks, months, or years. Foremost among such patient are human subjects.

In another aspect, the present disclosure provides a concentration control approach that periodically monitors Compound (1) exposure in a patient during the entire duration of treatment in the patient. Using this approach, a calculated adjustment of the dosage amount of Compound (1), or pharmaceutically acceptable salt thereof, may occur at any time, e.g., after about 4 weeks, after about 6 weeks, after about 8 weeks, after about 10 weeks, after about 12 weeks, after about 4 months, after about 6 months, after about 8 months, after about 10 months, or after about 1 year, or more, during treatment with Compound (1), or pharmaceutically acceptable salt thereof.

In another aspect, the disclosure provides a method of administering a therapeutically effective amount of Compound (1) to a patient in need thereof, the method comprising:

(a) administering an amount of Compound (1), or a pharmaceutically acceptable salt thereof, to the patient per day;

(b) obtaining a plasma sample from the patient after at least 5 days of administering according to (a);

(c) determining the plasma concentration of Compound (1) in the plasma sample obtained in (b); and (d) administering a recalculated amount of Compound (1), or a pharmaceutically acceptable salt thereof, in milligrams, to the patient per day as determined according to the Equation 1:

$$\text{new amount in mg} = SD \times \left(\frac{CMT}{PC}\right), \qquad \text{Equation 1}$$

wherein:

SD is the amount of Compound (1), or a pharmaceutically acceptable salt thereof, administered to the patient in (a) in mg;

CMT is the $C_{min\ target}$ in ng/mL;

$C_{min\ target}$=(target AUC ng h/mL×0.0341±20%)−1104±20%; and

PC is the plasma concentration in ng/mL of Compound (1) determined in (c).

In another aspect, the disclosure provides a method of administering a therapeutically effective amount of Compound (1) to a patient in need thereof, based on the plasma and/or cerebrospinal fluid (CSF) concentration of a biomarker, e.g., a PPAR-γ engagement biomarker, in a sample obtained from the patient.

In another aspect, the present disclosure provides a method of treating a disease or disorder in a patient in need thereof, the method comprising administering an initial dose of 1 to 20 milliliters, e.g., 1 milliliter, 2 milliliters, 4 milliliters, 5 milliliters, 6 milliliters, 7 milliliters, 8 milliliters, 9 milliliters, 10 milliliters, 11 milliliters, 12 milliliters, 13 milliliters, 14 milliliters, 15 milliliters, 16 milliliters, 17 milliliters, 18 milliliters, 19 milliliters, or 20 milliliters, of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μgh/mL.

In another aspect, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μg h/mL.

In another aspect, the present disclosure provides a method of treating a disease or disorder in a pediatric patient in need thereof, the method comprising administering an initial dose of 1 to 4 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the pediatric patient once per day if the plasma concentration of 5-[[4-[2-[5-(1-hydroxyethyl)pyridin-2-yl]ethoxy]phenyl]methyl]-1,3-thiazolidine-2,4-dione in the pediatric patient is less than 149 μg h/mL;

(b) administering a lower dose of the oral suspension to the pediatric patient once per day if the plasma concentration of 5-[[4-[2-[5-(1-hydroxyethyl)pyridin-2-yl]ethoxy]phenyl]methyl]-1,3-thiazolidine-2,4-dione in the pediatric patient is more than 241 μg h/mL; or (c) administering an unchanged dose of the oral suspension to the pediatric patient once per day if the plasma concentration of 5-[[4-[2-[5-(1-hydroxyethyl)pyridin-2-yl]ethoxy]phenyl]methyl]-1,3-thiazolidine-2,4-dione in the pediatric patient is between 150 μg h/mL and 240 μg h/mL.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

DETAILED DESCRIPTION

Figure 1:
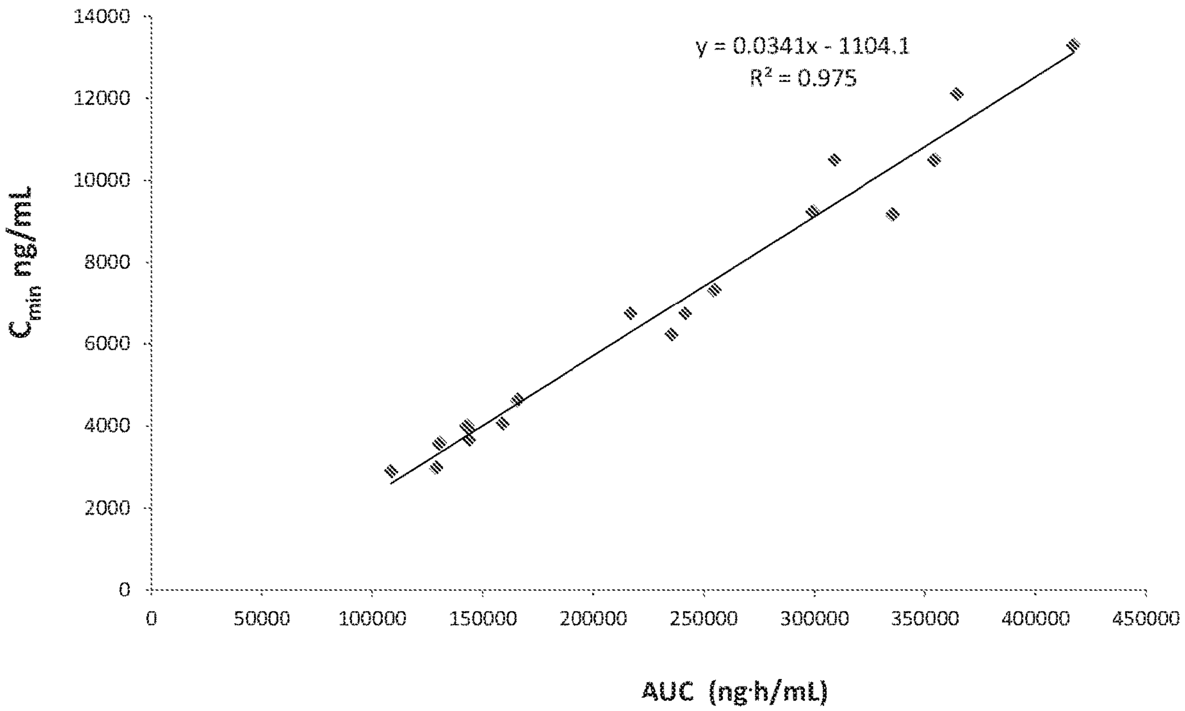
FIG. 1 is a line graph showing the relationship of trough value at steady state (labelled $C_{min}$ ng/mL in the figure) to area under the curve at steady state (labelled AUC ng h/mL in the figure) following daily oral dosing of 135 mg and 270 mg of 5-[[4-[2-[5-(1-hydroxyethyl)pyridin-2-yl]ethoxy]phenyl]methyl]-1,3-thiazolidine-2,4-dione hydrochloride to human patients.

I. Administration of Compound (1), or a Pharmaceutically Acceptable Salt Thereof The methods of the present disclosure comprise administering 5-[[4-[2-[5-(1-hydroxyethyl)pyridin-2-yl]ethoxy]phenyl]methyl]-1,3-thiazolidine-2,4-dione, or a pharmaceutically acceptable salt thereof, to a patient in need thereof. 5-[[4-[2-[5-(1-hydroxyethyl)pyridin-2-yl]ethoxy]phenyl]methyl]-1,3-thiazolidine-2,4-dione may also be referred to as 5-(4-(2-(5-(1-hydroxyethyl)pyridine-2-yl)ethoxy)benzyl)thiazolidine-2,4-dione, hydroxypioglitazone, hydroxy pioglitazone, or M-IV. See, e.g., Sohda et al., *Chem. Pharm. Bull.* 43(12):2168-2172 (1995) and Maeshiba et al., *Arzneim.-Forsch/Drug Res.* 47(1):29-35 (1997).

5-[[4-[2-[5-(1-hydroxyethyl)pyridin-2-yl]ethoxy]phenyl]methyl]-1,3-thiazolidine-2,4-dione has two chiral centers. One of them is the carbon atom in the 5-position of the thiazolidine-dione ring and the other asymmetric atom is at position 1 of the hydroxyethyl group as shown by the arrows:

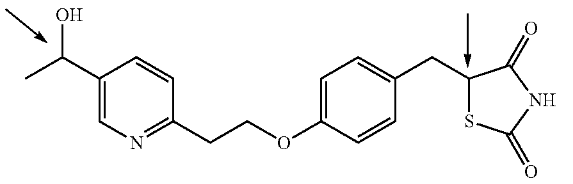 [SMILES: CC(O)c1ccc(CCOc2ccc(CC3SC(=O)NC3=O)cc2)nc1]

As used herein, the terms "5-[[4-[2-[5-(1-hydroxyethyl)pyridin-2-yl]ethoxy]phenyl]methyl]-1,3-thiazolidine-2,4-dione" or "Compound (1)" includes all possible stereoisomers, including enantiomers, see Compounds (2) to (5), below, and diastereomers, and mixtures thereof, including racemic and diastereomeric mixtures, of 5-[[4-[2-[5-(1-hydroxyethyl)pyridin-2-yl]ethoxy]phenyl]methyl]-1,3-thiazolidine-2,4-dione.

In one embodiment, the methods of the present disclosure comprise administering (R)-5-[[4-[2-[5-(R)-(1-hydroxyethyl)pyridin-2-yl]ethoxy]phenyl]methyl]-1,3-thiazolidine-2,4-dione (Compound (2)), or a pharmaceutically acceptable salt thereof, to a patient in need thereof.

Compound (2)

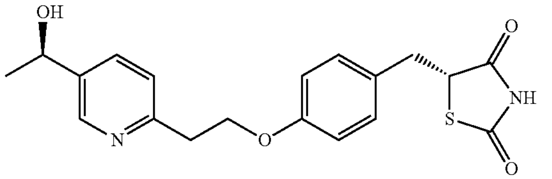

In another embodiment, the methods of the present disclosure comprise administering (R)-5-[[4-[2-[5-(S)-(1-hydroxyethyl)pyridin-2-yl]ethoxy]phenyl]methyl]-1,3-thiazolidine-2,4-dione (Compound (3)), or a pharmaceutically acceptable salt thereof, to a patient in need thereof.

Compound (3)

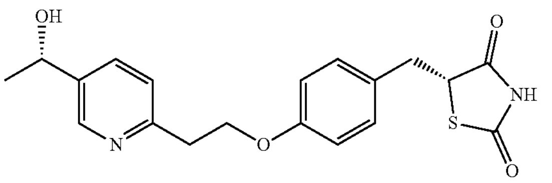

In another embodiment, the methods of the present disclosure comprise administering (S)-5-[[4-[2-[5-(R)-(1-hydroxyethyl)pyridin-2-yl]ethoxy]phenyl]methyl]-1,3-thiazolidine-2,4-dione (Compound (4)), or a pharmaceutically acceptable salt thereof, to a patient in need thereof, Compound (4)

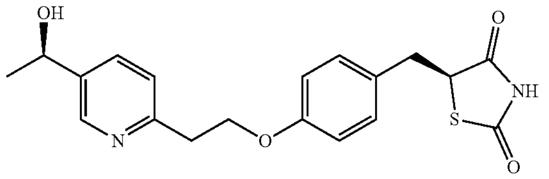

In another embodiment, methods of the present disclosure comprise administering (S)-5-[[4-[2-[5-(S)-(1-hydroxyethyl)pyridin-2-yl]ethoxy]phenyl]methyl]-1,3-thiazolidine-2,4-dione (Compound (5)), or a pharmaceutically acceptable salt thereof, to a patient in need thereof.

Compound (5)

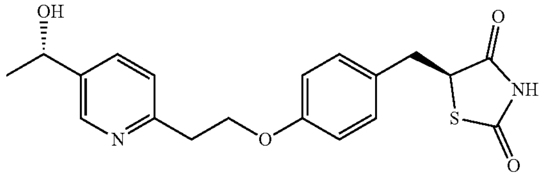

Compounds (2) to (5) have been prepared and isolated, see WO 2015/150476 A1, but their absolute (R/S) stereochemistry has not yet been determined. The retention time of each enantiomer has been measured by chiral HPLC.

Reference to Compounds (1) to (5) in the present disclosure is intended to designate these compounds as having hydrogen atoms which are predominantly in the form of its isotope $^{1}H$, i.e. no more than 1% of the total number of hydrogen atoms per mole of compound are in the form of the $^{2}H$ isotope (deuterium). In one embodiment, no more than 0.015% (which is the natural abundance of deuterium) of the total number of hydrogen atoms per mole of compound are in the form of the $^{2}H$ isotope (deuterium).

In one embodiment, the patient is administered a mixture comprising a non-equimolar amount of each of Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof.

In another embodiment, the patient is administered a mixture comprising each of Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof, in an amount of 20%±10% w/w.

In another embodiment, the patient is administered a mixture comprising each of Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof, in an amount of 25%±5% w/w.

In another embodiment, the patient is administered a mixture comprising each of Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof, wherein the mixture comprises an enantiomeric excess of one or more of Compound (2), Compound (3), Compound (4), and Compound (5).

In another embodiment, the patient is administered a mixture comprising an equimolar amount of each Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof, i.e., each compound, or pharmaceutically acceptable salt thereof, in an amount of 25% w/w.

In one embodiment, the patient is administered a mixture comprising on non-equimolar amount of Compound (2), or a pharmaceutically acceptable salt thereof; Compound (3), or a pharmaceutically acceptable salt thereof; Compound (4), or a pharmaceutically acceptable salt thereof; and Compound (5), or a pharmaceutically acceptable salt thereof, wherein the mixture is optically active.

In another embodiment, the mixture comprises:

(a) Compound (2), or a pharmaceutically acceptable salt thereof, and Compound (3), or a pharmaceutically acceptable salt thereof;

(b) Compound (4), or a pharmaceutically acceptable salt thereof, and Compound (5), or a pharmaceutically acceptable salt thereof:

(c) Compound (2), or a pharmaceutically acceptable salt thereof, and Compound (4), or a pharmaceutically acceptable salt thereof, and (d) Compound (3), or a pharmaceutically acceptable salt thereof, and Compound (5), wherein each compound, or a pharmaceutically acceptable salt thereof, is independently present in an equimolar or non-equimolar amount.

In another embodiment, the patient is administered the mixture (c) or the mixture (d) as these mixtures are defined above.

In another embodiment, the patient is administered a mixture consisting essentially of:

(a) Compound (2), or a pharmaceutically acceptable salt thereof, and Compound (3), or a pharmaceutically acceptable salt thereof, as the active agents;

(b) Compound (4), or a pharmaceutically acceptable salt thereof, and Compound (5), or a pharmaceutically acceptable salt thereof, as the active agents;

(c) Compound (2), or a pharmaceutically acceptable salt thereof, and Compound (4), or a pharmaceutically acceptable salt thereof, as the active agents; and (d) Compound (3), or a pharmaceutically acceptable salt thereof, and Compound (5), or a pharmaceutically acceptable salt thereof, as the active agents.

In another embodiment of the mixtures (a) to (d) mentioned above, the two compounds mentioned in each one of the mixtures are present in equimolar quantities. Said mixtures may comprise also minor amounts (e.g., less than 10 wt. %, less than 3 wt. %, less than 1 wt. %, and less than 0.1 wt. % of another stereoisomer of formula (1)). Said mixtures can also be enantiomerically enriched with respect to one or more Compounds (2), (3), (4), and (5).

In another aspect of the disclosure, a pharmaceutically acceptable salt of Compound (1) is administered to the patient. Suitable pharmaceutically acceptable salts include, for example, pharmaceutically acceptable acid addition salts of Compound (1) prepared from the following acids: formic, acetic, propionic, benzoic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, xinafoic, tartaric, trifluoroacetic, pamoic, propionic, anthranilic, mesylic, napadisylate, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. In an embodiment, the pharmaceutically acceptable salts include the salts of hydrochloric acid and hydrobromic acid. In one embodiment, the pharmaceutically acceptable salt of Compound (1) is the salt of the hydrochloric acid, e.g., 5-[[4-[2-[5-(1-hydroxyethyl)pyridin-2-yl]ethoxy]phenyl]methyl]-1,3-thiazolidine-2,4-dione hydrochloride.

5-[[4-[2-[5-(1-hydroxyethyl)pyridin-2-yl]ethoxy]phenyl]methyl]-1,3-thiazolidine-2,4-dione can be prepared by any suitable method known in the art, such as by the processes described in WO 2015/150476 A1 and WO 2018/116281 A1. 5-[[4-[2-[5-(1-hydroxyethyl)pyridin-2-yl]ethoxy]phenyl]methyl]-1,3-thiazolidine-2,4-dione is also commercially available from, for example, Santa Cruz Biotechnology and Toronto Research Chemicals (Toronto, Ontario, Canada).

II. Methods and Uses of the Disclosure

In one embodiment, the present disclosure provides methods of treating a disease or disorder in a patient in need thereof, the method comprising administering 5-[[4-[2-[5-(1-hydroxyethyl)pyridin-2-yl]ethoxy]phenyl]methyl]-1,3-thiazolidine-2,4-dione (Compound (1)), or a pharmaceutically acceptable salt thereof, to the patient, wherein:

(i) the $AUC_{ss}$ of Compound (1) in plasma from the patient is about 34 μg h/mL to about 300 μg h/mL;

(ii) the $C_{min\ ss}$ of Compound (1) in plasma from the patient is about 55 ng/mL to about 9126 ng/mL; or (iii) the $AUC_{ss}$ of Compound (1) in plasma from the patient is about 34 μg h/mL to about 300 μg h/mL, and the $C_{min\ ss}$ of Compound (1) in plasma from the patient is about 55 to about 9126 ng/mL; and the $AUC_{ss}$ of (i), the $C_{min\ ss}$ of (ii), or the $AUC_{ss}$ and $C_{min\ ss}$ of (iii) is measured after at least five days of administering Compound (1), or a pharmaceutically acceptable salt thereof, to the patient per day. In another embodiment, the $AUC_{ss}$ of (i), the $C_{min\ ss}$ of (ii), or the $AUC_{ss}$ and $C_{min\ ss}$ of (iii) is measured after 3-15 days, e.g., 3, 4, 5, 6, 7, 8, 9, 10, 11, 12, 13, 14, or 15 days, of administering Compound (1), or a pharmaceutically acceptable salt thereof, to the patient once per day. In another embodiment, the $AUC_{ss}$ of (i), the $C_{min\ ss}$ of (ii), or the $AUC_{ss}$ and $C_{min\ ss}$ of (iii) is measured after 4 days of administering Compound (1), or a pharmaceutically acceptable salt thereof, to the patient once per day. In another embodiment, the $AUC_{ss}$ of (i), the $C_{min\ ss}$ of (ii), or the $AUC_{ss}$ and $C_{min\ ss}$ of (iii) is measured after 5 days of administering Compound (1), or a pharmaceutically acceptable salt thereof, to the patient once per day.

In another embodiment, the present disclosure provides methods of treating a disease or disorder, e.g., a CNS disease or disorder, in a patient in need thereof, the method comprising administering 5-[[4-[2-[5-(1-hydroxyethyl)pyridin-2-yl]ethoxy]phenyl]methyl]-1,3-thiazolidine-2,4-dione (Compound (1)), or a pharmaceutically acceptable salt thereof, to the patient, wherein:

(i) the $AUC_{ss}$ of Compound (1) in plasma from the patient is about 100 μg h/mL to about 300 μg h/mL;

(ii) the $C_{min\ ss}$ of Compound (1) in plasma from the patient is about 2306 ng/mL to about 9126 ng/mL; or (iii) the $AUC_{ss}$ of Compound (1) in plasma from the patient is about 100 μg h/mL to about 300 μg h/mL, and the $C_{min\ ss}$ of Compound (1) in plasma from the patient is about 2306 ng/mL to about 9126 ng/mL; and the $AUC_{ss}$ of (i), the $C_{min\ ss}$ of (ii), or the $AUC_{ss}$ and $C_{min\ ss}$ of (iii) is measured after at least five days of administering Compound (1), or a pharmaceutically acceptable salt thereof, to the patient per day. In another embodiment, the $AUC_{ss}$ of (i), the $C_{min\ ss}$ of (ii), or the $AUC_{ss}$ and $C_{min\ ss}$ of (iii) is measured after 3-15 days, e.g., 3, 4, 5, 6, 7, 8, 9, 10, 11, 12, 13, 14, or 15 days, of administering Compound (1), or a pharmaceutically acceptable salt thereof, to the patient once per day. In another embodiment, the $AUC_{ss}$ of (i), the $C_{min\ ss}$ of (ii), or the $AUC_{ss}$ and $C_{min\ ss}$ of (iii) is measured after 4 days of administering Compound (1), or a pharmaceutically acceptable salt thereof, to the patient once per day. In another embodiment, the $AUC_{ss}$ of (i), the $C_{min\ ss}$ of (ii), or the $AUC_{ss}$ and $C_{min\ ss}$ of (iii) is measured after 5 days of administering Compound (1), or a pharmaceutically acceptable salt thereof, to the patient once per day.

In another embodiment, the $AUC_{ss}$ of Compound (1) is about 100 μg h/mL to about 300 μg h/mL for treating a disease or disorder.

In another embodiment, the $AUC_{ss}$ of Compound (1) is about 100 μg h/mL to about 200 μg h/mL for treating a disease or disorder.

In another embodiment, the $AUC_{ss}$ of Compound (1) is about 130 μg h/mL to about 200 μg h/mL for treating a disease or disorder.

In another embodiment, the $AUC_{ss}$ of Compound (1) is about 150 μg h/mL to about 250 μg h/mL for treating a disease or disorder.

In another embodiment, the $AUC_{ss}$ of Compound (1) is about 175 μg h/mL to about 225 μg h/mL for treating a disease or disorder.

In another embodiment, the $AUC_{ss}$ of Compound (1) is about 50 μg h/mL to about 250 μg h/mL for treating a disease or disorder.

In another embodiment, the $AUC_{ss}$ of Compound (1) is about 100 μg h/mL to about 200 μg h/mL for treating a disease or disorder.

In another embodiment, the $AUC_{ss}$ of Compound (1) is about 125 μg h/mL to about 175 μg h/mL for treating a disease or disorder.

In another embodiment, the $AUC_{ss}$ of Compound (1) is about 100 μg h/mL. about 110 μg h/mL. about 120 μg h/mL. about 130 μg h/mL. about 140 μg h/mL. about 150 μg h/mL. about 160 μg h/mL. about 170 μg h/mL. about 180 μg h/mL. or about 190 μg h/mL for treating a disease or disorder.

In another embodiment, the $AUC_{ss}$ of Compound (1) is about 200 μg h/mL for treating a disease or disorder.

In another embodiment, the $C_{min\ ss}$ of Compound (1) is about 2306 ng/mL to about 9126 ng/mL for treating a disease or disorder.

In another embodiment, the $C_{min\ ss}$ of Compound (1) is about 3329 ng/mL to about 5716 ng/mL for treating a disease or disorder.

In another embodiment, the $C_{min\ ss}$ of Compound (1) is about 401 ng/mL to about 7421 ng/mL for treating a disease or disorder.

In another embodiment, the $C_{min\ ss}$ of Compound (1) is about 4864 ng/mL to about 6569 ng/mL for treating a disease or disorder.

In another embodiment, the $C_{min\ ss}$ of Compound (1) is about 5034 ng/mL to about 6569 ng/mL for treating a disease or disorder.

In another embodiment, the $C_{min\ ss}$ of Compound (1) is about 5375 ng/mL to about 6569 ng/mL for treating a disease or disorder.

In another embodiment, the $C_{min\ ss}$ of Compound (1) is about 2306 ng/mL, about 2647 ng/mL, about 2988 ng/mL, about 3329 ng/mL, about 3670 ng/mL, about 4011 ng/mL, about 4352 ng/mL, about 4693 ng/mL, about 4864 ng/mL, about 5034 ng/mL, about 5375 ng/mL, about 5716 ng/mL, about 6569 ng/mL, about 7421 ng/mL, about 8274 ng/mL, or about 9126 ng/mL for treating a disease or disorder.

In another embodiment, the $C_{min\ ss}$ of Compound (1) is about 1595 ng/mL to about 7421 ng/mL for treating a disease or disorder.

In another embodiment, the $C_{min\ ss}$ of Compound (1) is about 2306 ng/mL to about 5716 ng/mL for treating a disease or disorder.

In another embodiment, the $C_{min\ ss}$ of Compound (1) is about 3158 ng/mL to about 4863 ng/mL for treating a disease or disorder.

In another embodiment, the $C_{min\ ss}$ of Compound (1) is about 4352 ng/mL for treating a disease or disorder.

In another embodiment, the $C_{min\ ss}$ of Compound (1) is about 5716 ng/mL for treating a disease or disorder.

In another embodiment, the present disclosure provides methods of treating a disease or disorder, e.g., a non-CNS disease or disorder or a disease or disorder in a child, in a patient in need thereof, the method comprising administering 5-[[4-[2-[5-(1-hydroxyethyl)pyridin-2-yl]ethoxy]phenyl]methyl]-1,3-thiazolidine-2,4-dione (Compound (1)), or a pharmaceutically acceptable salt thereof, to the patient, wherein:

(i) the $AUC_{ss}$ of Compound (1) in plasma from the patient is about 34 μg h/mL to about 80 μg h/mL;

(ii) the $C_{min\ ss}$ of Compound (1) in plasma from the patient is about 55 ng/mL to about 1624 ng/mL; or (iii) the $AUC_{ss}$ of Compound (1) in plasma from the patient is about 34 μg h/mL to about 80 μg h/mL, and the $C_{min\ ss}$ of Compound (1) in plasma from the patient is about 55 ng/mL to about 1624 ng/mL; and the $AUC_{ss}$ of (i), the $C_{min\ ss}$ of (ii), or the $AUC_{ss}$ and $C_{min\ ss}$ of (iii) is measured after at least five days of administering Compound (1), or a pharmaceutically acceptable salt thereof, to the patient per day.

In another embodiment, the $AUC_{ss}$ of Compound (1) is about 40 μg h/mL for a disease or disorder.

In another embodiment, the $AUC_{ss}$ of Compound (1) is about 50 μg h/mL for a disease or disorder.

In another embodiment, the $AUC_{ss}$ of Compound (1) is about 60 μg h/mL for disease or disorder.

In another embodiment, the $AUC_{ss}$ of Compound (1) is about 70 μg h/mL for a disease or disorder.

In another embodiment, the $AUC_{ss}$ of Compound (1) is about 80 μg h/mL for a disease or disorder.

In another embodiment, the $AUC_{ss}$, $C_{min\ ss}$, or $AUC_{ss}$ and $C_{min\ ss}$ is measured after at least four days.

In another embodiment, the $AUC_{ss}$, $C_{min\ ss}$, or $AUC_{ss}$ and $C_{min\ ss}$ is measured after at least seven days.

In another embodiment, the $AUC_{ss}$, $C_{min\ ss}$, or $AUC_{ss}$ and $C_{min\ ss}$ is measured after at least ten days.

In another embodiment, the $AUC_{ss}$, $C_{min\ ss}$, or $AUC_{ss}$ and $C_{min\ ss}$ is measured after at least fourteen days.

In another embodiment, the present disclosure provides a method of treating a disease or disorder, e.g., a CNS disease or disorder, in a patient in need thereof, the method comprising administering 5-[[4-[2-[5-(1-hydroxyethyl)pyridin-2-yl]ethoxy]phenyl]methyl]-1,3-thiazolidine-2,4-dione (Compound (1)), or a pharmaceutically acceptable salt thereof, to the patient, wherein:

(a) the $AUC_{ss}$ of Compound (1) in plasma from the patient is about 30 μg h/mL to about 300 μg h/mL; and (b) the $AUC_{ss}$ is measured after administering Compound (1), or a pharmaceutically acceptable salt thereof, to the patient once per day for five or more days.

In another embodiment, the $AUC_{ss}$ of Compound (1) in plasma from the patient is about 50 μg h/mL to about 250 μg h/mL.

In another embodiment, the $AUC_{ss}$ of Compound (1) in plasma from the patient is about 50 μg h/mL to about 200 μg h/mL.

In another embodiment, the $AUC_{ss}$ of Compound (1) in plasma from the patient is about 50 μg h/mL to about 175 μg h/mL.

In another embodiment, the $AUC_{ss}$ of Compound (1) in plasma from the patient is about 50 μg h/mL to about 150 μg h/mL.

In another embodiment, the $AUC_{ss}$ of Compound (1) in plasma from the patient is about 50 μg h/mL to about 125 μg h/mL.

In another embodiment, the $AUC_{ss}$ of Compound (1) in plasma from the patient is about 50 μg h/mL to about 100 μg h/mL.

In another embodiment, the $AUC_{ss}$ of Compound (1) in plasma from the patient is about 75 μg h/mL to about 225 μg h/mL.

In another embodiment, the $AUC_{ss}$ of Compound (1) in plasma from the patient is about 100 μg h/mL to about 200 μg h/mL.

In another embodiment, the $AUC_{ss}$ of Compound (1) in plasma from the patient is about 150 μg h/mL to about 190 μg h/mL.

In another embodiment, the $AUC_{ss}$ of Compound (1) in plasma from the patient is about 180 μg h/mL to about 220 μg h/mL.

In another embodiment, the $AUC_{ss}$ of Compound (1) in plasma from the patient is about 190 μg h/mL to about 210 μg h/mL.

In another embodiment, the $AUC_{ss}$ of Compound (1) in plasma from the patient is about 30 μg h/mL, about 40 μg h/mL, about 50 μg h/mL, about 60 μg h/mL, about 70 μg h/mL, about 80 μg h/mL, about 90 μg h/mL, about 100 μg h/mL, about 110 μg h/mL, about 120 μg h/mL, about 130 μg h/mL, about 140 μg h/mL, about 150 μg h/mL, about 160 μg h/mL, about 170 μg h/mL, about 180 μg h/mL, about 190 μg h/mL, about 200 μg h/mL, about 210 μg h/mL, or about 220 μg h/mL.

In another embodiment, the $AUC_{ss}$ is measured after administering Compound (1), or a pharmaceutically acceptable salt thereof, to the patient once per day for 6, 7, 8, 9, 10, 11, 12, 13, or 14 days.

In another embodiment, 5-[[4-[2-[5-(1-hydroxyethyl)pyridin-2-yl]ethoxy]phenyl]methyl]-1,3-thiazolidine-2,4-dione hydrochloride is administered to the patient in need thereof. 5-[[4-[2-[5-(1-hydroxyethyl)pyridin-2-yl]ethoxy]phenyl]methyl]-1,3-thiazolidine-2,4-dione hydrochloride is also referred to herein as "Compound (1) HCl."

In another embodiment, the Compound (1) HCl is administered to the patient as a suspension comprising about 15 mg of Compound (1) HCl per mL.

In another embodiment, the Compound (1) HCl is administered to the patient as a tablet, capsule, or other solid form comprising about 30 mg of Compound (1) HCl, about 60 mg of Compound (1) HCl, or about 90 mg of Compound (1) HCl.

In another aspect, the disclosure provides a method of administering a therapeutically effective amount of Compound (1) to a patient in need thereof, the method comprising:

(a) administering an amount of Compound (1), or a pharmaceutically acceptable salt thereof, to the patient per day;

(b) obtaining a plasma sample from the patient after at least 5 days of administering according to (a);

(c) determining the plasma concentration of Compound (1) in the plasma sample obtained in (b); and (d) administering a recalculated amount of Compound (1), or a pharmaceutically acceptable salt thereof, in milligrams, to the patient per day as determined according to the Equation 1:

$$\text{new amount in mg} = SD \times \left(\frac{CMT}{PC}\right), \qquad \text{Equation 1}$$

wherein:

SD is the amount of Compound (1), or a pharmaceutically acceptable salt thereof, administered to the patient in (a) in mg;

CMT is the $C_{min\ target}$ in ng/mL;

$C_{min\ target}$=(target AUC ng h/mL×0.0341±20%)−1104±20%; and

PC is the plasma concentration in ng/mL of Compound (1) determined in (c).

In another aspect, the disclosure provides a method of administering a therapeutically effective amount of Compound (1) to a patient in need thereof, the method comprising:

(a) administering an amount of Compound (1), or a pharmaceutically acceptable salt thereof, to the patient per day;

(b) obtaining a plasma sample from the patient after 3-15 days, e.g., 3, 4, 5, 6, 7, 8, 9, 10, 11, 12, 13, or 14 days. of administering according to (a);

(c) determining the plasma concentration of Compound (1) in the plasma sample obtained in (b); and (d) administering a recalculated amount of Compound (1), or a pharmaceutically acceptable salt thereof, in milligrams, to the patient per day as determined according to the Equation 1 as above.

In another embodiment, CMT or ($C_{min\ target}$)=(target AUC ng h/mL×0.0341±10%)−1104±10% in Equation 1.

In another embodiment, CMT or ($C_{min\ target}$)=(target AUC ng h/mL×0.0341±5%)−1104±5% in Equation 1.

In another embodiment, CMT or ($C_{min\ target}$)=(target AUC ng h/mL×0.0341)−1104 in Equation 1.

In another embodiment, the target AUC is about 100 μgh/mL to about 300 μg h/mL.

In another embodiment, the target AUC is about 100 μgh/mL to about 200 μg h/mL.

In another embodiment, the target AUC is about 100 μgh/mL, about 110 μgh/mL, about 120 μgh/mL, about 130 μgh/mL, about 140 μgh/mL, about 150 μgh/mL, about 160 μgh/mL, about 170 μg h/mL, about 180 μgh/mL, about 190 μg h/mL, or about 200 μg h/mL.

In another embodiment, the amount of Compound (1), or a pharmaceutically acceptable salt thereof, administered to the patient in (a) is about 100 mg to about 200 mg.

In another embodiment, the amount of Compound (1), or a pharmaceutically acceptable salt thereof, administered to the patient in (a) is about 90, about 100 mg, about 110 mg, about 120 mg, about 130 mg, about 140 mg, about 150 mg, about 160 mg, about 170 mg, about 180 mg, about 190 mg, about 200 mg, or about 210 mg.

In another embodiment, the target AUC is about 200 μgh/mL and the amount of Compound (1), or a pharmaceutically acceptable salt thereof, administered to the patient in (a) is about 150 mg.

In another embodiment, the target AUC is about 200 μgh/mL and the amount of Compound (1), or a pharmaceutically acceptable salt thereof, administered to the patient in (a) is about 1850 mg.

In another embodiment, the present disclosure provides a method of administering a therapeutically effective amount of Compound (1) to a patient in need thereof, the method comprising:

(a) administering about 90 mg to about 210 mg of Compound (1), or a pharmaceutically acceptable salt thereof, to the patient per day;
(b) obtaining a plasma sample from the patient after at least 5 days of administering according to (a);
(c) determining the plasma concentration of Compound (1) in the plasma sample obtained in (b); and
(d) administering a recalculated amount of Compound (1), or a pharmaceutically acceptable salt thereof, in milligrams, to the patient per day as determined according to the Equation 2:

$$\text{new amount in mg} = PD \times \left(\frac{5716}{PC}\right), \qquad \text{Equation 2}$$

wherein PD is the amount of Compound (1), or a pharmaceutically acceptable salt thereof, administered to the patient in (a); and PC is the plasma concentration in ng/mL of Compound (1) determined in (c).

In another embodiment, the present disclosure provides a method of administering a therapeutically effective amount of Compound (1) to a patient in need thereof, the method comprising:

(a) administering about 90 mg to about 210 mg of Compound (1), or a pharmaceutically acceptable salt thereof, to the patient per day;
(b) obtaining a plasma sample from the patient after 3-15 days, e.g., 3, 4, 5, 6, 7, 8, 9, 10, 11, 12, 13, 14, or 15 days, of administering according to (a);
(c) determining the plasma concentration of Compound (1) in the plasma sample obtained in (b); and
(d) administering a recalculated amount of Compound (1), or a pharmaceutically acceptable salt thereof, in milligrams, to the patient per day as determined according to the Equation 2 as above.

In another embodiment, the plasma sample is obtained from the patient after at least 7 days of administering according to (a).

In another embodiment, a plasma sample is obtained from the patient after at least 10 days of administering according to (a).

In another embodiment, a plasma sample is obtained from the patient after at least 14 days of administering according to (a).

In another embodiment, the Compound (1), or a pharmaceutically acceptable salt thereof, is administered orally to the patient in (a) and (d).

In another embodiment, Compound (1) HCl is administered to the patient per day in (a) and (d).

In another embodiment, about 90 mg of Compound (1), or a pharmaceutically acceptable salt thereof, is administered to the patient per day in (a).

In another embodiment, about 120 mg of Compound (1), or a pharmaceutically acceptable salt thereof, is administered to the patient per day in (a).

In another embodiment, about 150 mg of Compound (1), or a pharmaceutically acceptable salt thereof, is administered to the patient per day in (a).

In another embodiment, about 180 mg of Compound (1), or a pharmaceutically acceptable salt thereof, is administered to the patient per day in (a).

In another embodiment, about 210 mg of Compound (1), or a pharmaceutically acceptable salt thereof, is administered to the patient per day in (a).

In another embodiment, about 150 mg of Compound (1) HCl is administered to the patient per day in (a).

In another embodiment, a recalculated amount of Compound (1) HCl is administered to the patient per day in (d).

In another embodiment, the Compound (1) HCl is administered to the patient in (a) and (d) as a suspension comprising about 15 mg of Compound (1) HCl per mL.

In another embodiment, the Compound (1) HCl is administered to the patient in (a) and (d) as a tablet, capsule, or other solid form comprising about 30 mg of Compound (1) HCl, about 60 mg of Compound (1) HCl, or about 90 mg of Compound (1) HCl.

In another embodiment, the disclosure provides a method of orally administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising:

(a) orally administering about 150 mg of Compound (1) HCl to the patient per day as a suspension comprising about 15 mg of Compound (1) HCl per mL;
(b) obtaining a plasma sample from the patient after at least 14 days of administering according to (a);
(c) determining the plasma concentration of 5-[[4-[2-[5-(1-hydroxyethyl)pyridin-2-yl]ethoxy]phenyl]methyl]-1,3-thiazolidine-2,4-dione in the plasma sample obtained in (b); and
(d) orally administering a new amount of Compound (1) HCl in milligrams to the patient per day according to the Equation 3:

$$\text{new amount in mg} = 150 \times \left(\frac{5716}{PC}\right), \qquad \text{Equation 3}$$

wherein PC is the plasma concentration in ng/mL of 5-[[4-[2-[5-(1-hydroxyethyl)pyridin-2-yl]ethoxy]phenyl]methyl]-1,3-thiazolidine-2,4-dione determined in (c).

In another embodiment, the disclosure provides a method of administering a therapeutically effective amount of Compound (1) to a patient in need thereof, the method comprising:

(a) determining the plasma or cerebrospinal fluid (CSF) concentration of a biomarker in a sample obtained from the patient;

(b) administering an amount of Compound (1), or a pharmaceutically acceptable salt thereof, to the patient per day;
(c) obtaining a plasma or CSF sample from the patient after at least 5 days of administering according to (b);
(d) determining the plasma or CSF concentration of the biomarker in the plasma or CSF sample obtained in (c); and
(e) administering a recalculated amound of Compound (1), or a pharmaceutically acceptable salt thereof, in milligrams, based on the biomarker concentration in the plasma or CSF sample obtained in (d).

In another embodiment, the biomarker is a PPAR-γ engagement biomarker in the plasma.

In another embodiment, the biomarker is a PPAR-γ engagement biomarker in the CSF.

In another embodiment, the PPAR-γ engagement biomarker in the CSF is adiponectin or FABP4, and the concentration of adiponectin and/or FABP4 increases as a result of administering Compound (1), or a pharmaceutically acceptable salt thereof, to the patient.

In another embodiment, the biomarker is an inflammatory biomarker in the CSF.

In another embodiment, the inflammatory biomarker in the CSF is IP10, IL6, IL8, MMP9, MMP2 or MCP-1, and the concentration of IP10, IL6, IL8, MMP-9; MMp-2, and/or MCP-1 decreases as a result of administering Compound (1), or a pharmaceutically acceptable salt thereof, to the patient.

In another embodiment, the disclosure provides a method of administering a therapeutically effective amount of Compound (1) to a patient in need thereof, the method comprising determining the plasma and/or CSF concentration of a PPAR gamma engagement biomarker, e.g., adiponectin, FABP4, PPAR gamma, PGC-1 alpha, anti-inflammatory markers, NfKb dependent genes such as IL-1, IL-6, VCAM-1, ICAM-1, IL-8; TNF-alpha; MMP-9; MMP-2 and IFN, survival biomarkers such as BCL-2, and oligodendrocyte differentation such as Olig2, in a sample obtained from the patient to give a baseline concentration of the biomarker; and (a) administering an amount of Compound (1), or a pharmaceutically acceptable salt thereof, to the patient per day;
(b) obtaining a plasma and/or CSF sample from the patient after 5 days or more of administering according to (a);
(c) determining the plasma and/or CSF concentration of biomarker in the plasma and/or CSF sample obtained in (b); and
(d) administering a recalculated amount of Compound (1), or a pharmaceutically acceptable salt thereof, in milligrams, based on the concentration of the biomaker in the plasma and/or CSF sample obtained in (c), wherein:
(i) an increase in the biomarker of about 200% or less in (c) relative to the baseline concentration of the biomarker comprises administering a greater amount of Compound (1), or a pharmaceutically acceptable salt thereof, in mg per day, to the patient;
(ii) an increase in the biomarker of about 600% or more in (c) relative to the baseline concentration of adiponectin comprises administering a lesser amount of Compound (1), or a pharmaceutically acceptable salt thereof, in mg per day, to the patient; and
(iii) an increase in the biomarker of about 200% to about 600% in (c) relative to the baseline concentration of the biomarker comprises administering the same amount of Compound (1), or a pharmaceutically acceptable salt thereof, in mg per day, to the patient.

In another embodiment, the plasma concentration of the biomarker is measured in the sample obtained from the patient.

In another aspect, the disclosure provides a method of administering a therapeutically effective amount of Compound (1) to a patient in need thereof, the method comprising determining the plasma and/or CSF concentration of adiponectin in a sample obtained from the patient to give a baseline concentration of adiponectin; and (a) administering an amount of Compound (1), or a pharmaceutically acceptable salt thereof, to the patient per day;
(b) obtaining a plasma and/or CSF sample from the patient after at least 5 days of administering according to (a);
(c) determining the plasma and/or CSF concentration of adiponectin in the plasma and/or CSF sample obtained in (b); and
(d) administering a recalculated amount of Compound (1), or a pharmaceutically acceptable salt thereof, in milligrams, based on the concentration of adiponectin in the plasma and/or CSF sample obtained in (c), wherein:
(i) an increase in adiponectin of about 200% or less in (c) relative to the baseline concentration of adiponectin comprises administering a greater amount of Compound (1), or a pharmaceutically acceptable salt thereof, in mg per day, to the patient;
(ii) an increase in adiponectin of about 600% or more in (c) relative to the baseline concentration of adiponectin comprises administering a lesser amount of Compound (1), or a pharmaceutically acceptable salt thereof, in mg per day, to the patient; and
(iii) an increase in adiponectin of about 200% to about 600% in (c) relative to the baseline concentration of adiponectin comprises administering the same amount of Compound (1), or a pharmaceutically acceptable salt thereof, in mg per day, to the patient.

In another embodiment, the plasma concentration of adiponectin is measured in the sample obtained from the patient.

In another embodiment, an increase in adiponectin of about 200% to about 300% in (c) relative to (a) comprises administering the same amount of Compound (1), or a pharmaceutically acceptable salt thereof, in mg per day, to the patient.

In another embodiment, the Compound (1), or pharmaceutically acceptable salt thereof, e.g., 5-[[4-[2-[5-(1-hydroxyethyl)pyridin-2-yl]ethoxy]phenyl]methyl]-1,3-thiazolidine-2,4-dione hydrochloride, is administered to a patient in (a) and (d) having a disease or disorder.

In another embodiment, the disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising:

(a) administering 5 to 20 milliliters of an oral suspension of 5-[[4-[2-[5-(1-hydroxyethyl)pyridin-2-yl]ethoxy]phenyl]methyl]-1,3-thiazolidine-2,4-dione hydrochloride to the patient per day, wherein the oral suspension comprises 15 mg of 5-[[4-[2-[5-(1-hydroxyethyl)pyridin-2-yl]ethoxy]phenyl]methyl]-1,3-thiazolidine-2,4-dione hydrochloride per mL;

(b) obtaining a plasma sample from the patient following 5 days or more of administering according to (a);

(c) determining the $C_{min\ ss}$ of 5-[[4-[2-[5-(1-hydroxyethyl)pyridin-2-yl]ethoxy]phenyl]methyl]-1,3-thiazolidine-2,4-dione in the plasma sample obtained in (b); and (d) administering a recalculated amount, in milliliters, of the oral suspension to the patient per day as determined according to the Equation 4:

$$Dose_{V1} = Dose_{pre-V1} x \frac{C_{min_{TAR}}}{C_{min_{V1}}}, \quad \text{Equation 4}$$

wherein:

$Dose_{V1}$ is the recalculated amount, in milliliters, of the oral suspension administered to the patient per day in (d);

$Dose_{pre-V1}$ is the amount, in milliliters, of the oral suspension administered to the patient in (a);

$C_{min_{V1}}$ is the $C_{min\ ss}$, in ng/mL, of 5-[[4-[2-[5-(1-hydroxyethyl)pyridin-2-yl]ethoxy]phenyl]methyl]-1,3-thiazolidine-2,4-dione determined in (c) taken 22-26 hours after the last administration; and $C_{min_{TAR}}$ is the targeted concentration in ng/mL of 5 5-[[4-[2-[5-(1-hydroxyethyl)pyridin-2-yl]ethoxy]phenyl]methyl]-1,3-thiazolidine-2,4-dione, wherein:

(A) $C_{min_{TAR}}$ is calculated according to Equation 5A:

$$C_{min_{TAR}}=7700-(88.5\times Dose_{pre-V1}) \quad \text{Equation 5A}$$

if the plasma sample in (b) was obtained 18 hours to 19.9 hours after the last administration of the oral suspension in (a);

(B) $C_{min_{TAR}}$ is calculated according to Equation 5B:

$$C_{min_{TAR}}=7440-(103.4\times Dose_{pre-V1}) \quad \text{Equation 5B}$$

if the plasma sample in (b) was obtained 20 hours to 21.9 hours after the last administration of the oral suspension in (a);

(C) $C_{min_{TAR}}$ is 5716 if the plasma sample in (b) was obtained 22 hours to 25.9 hours after the last administration of the oral suspension in (a);

(D) $C_{min_{TAR}}$ is calculated according to Equation 5D:

$$C_{min_{TAR}}=6740-(138.6\times Dose_{pre-V1}) \quad \text{Equation 5D}$$

if the plasma sample in (b) was obtained 26 hours to 27.9 hours after the last administration of the oral suspension in (a); or (E) $C_{min_{TAR}}$ is calculated according to Equation 5E:

$$C_{minTAR}=6520-(148.0\times Dose_{pre-V1}) \quad \text{Equation 5E}$$

if the plasma sample in (b) was obtained 28 hours to 30 hours after the last administration of the oral suspension in (a).

In another embodiment in connection with the embodiment immediately above, the disclosure provides a method further comprising:

(i) obtaining a plasma sample from the patient following 5 days or more of administering the recalculated amount, in milliliters, of the oral suspension of 5-[[4-[2-[5-(1-hydroxyethyl)pyridin-2-yl]ethoxy]phenyl]methyl]-1,3-thiazolidine-2,4-dione hydrochloride to the patient per day in (d);

(ii) determining the $C_{min_{calcd}}$, in ng/mL, of 5-[[4-[2-[5-(1-hydroxyethyl)pyridin-2-yl]ethoxy]phenyl]methyl]-1,3-thiazolidine-2,4-dione in the plasma sample obtained in (i) according to Equation 6:

$$C_{min_{calcd}} = \frac{Dose_{V1} \times C_{min_{V2}}}{Dose_{last\ taken}}; \quad \text{Equation 6}$$

(iii) determining the $AUC_{Calcd}$, in μg h/mL, of 5-[[4-[2-[5-(1-hydroxyethyl)pyridin-2-yl]ethoxy]phenyl]methyl]-1,3-thiazolidine-2,4-dione based on the $C_{min_{calcd}}$ determined in (ii), wherein:

(A) the $AUC_{Calcd}$ is calculated according to Equation 7A:

$$AUC_{Calcd} = \frac{C_{min_{calcd}} + (88.5 \times Dose_{last\ taken})}{38.5}, \quad \text{Equation 7A}$$

if the plasma sample in (i) was obtained between 18 hours to 19.9 hours after the last administration of the oral suspension;

(B) the $AUC_{Calcd}$ is calculated according to Equation 7B:

$$AUC_{Calcd} = \frac{C_{min_{calcd}} + (103.4 \times Dose_{last\ taken})}{37.2}, \quad \text{Equation 7B}$$

if the plasma sample in (i) was obtained 20 hours to 21.9 hours after the last administration of the oral suspension;

(C) the $AUC_{Calcd}$ is calculated according to Equation 7C:

$$AUC_{Calcd} = \frac{C_{min_{calcd}} + 1104.1}{34.1}, \quad \text{Equation 7C}$$

if the plasma sample in (i) was obtained 22 hours to 25.9 hours after the last administration of the oral suspension;

(D) the $AUC_{Calcd}$ is calculated according to Equation 7D:

$$AUC_{Calcd} = \frac{C_{min_{calcd}} + (138.6 \times Dose_{last\ taken})}{33.7}, \quad \text{Equation 7D}$$

if the plasma sample in (i) was obtained 26 hours to 27.9 hours after the last administration of the oral suspension; or (E) the $AUC_{Calcd}$ is calculated according to Equation 7E:

$$AUC_{Calcd} = \frac{C_{min_{calcd}} + (148 \times Dose_{last\ taken})}{32.6}, \quad \text{Equation 7E}$$

if the plasma sample in (i) was obtained 28 hours to 30 hours after the last administration of the oral suspension; and (iv) administering the same recalculated amount, in milliliters, of the oral suspension to the patient per day as in (i) for 5 days or more if the $AUC_{Calcd}$ is 150 to 240 μg h/mL and, optionally, repeating (i)-(iii); or (v) administering an new amount, in milliliters, of the oral suspension to the patient per day in (i) if the $AUC_{Calcd}$ is less than 150 or more than 240 μgh/mL.

In another aspect, the present disclosure provides a method of treating a disease or disorder in a patient in need thereof, the method comprising administering an initial dose of 1 to 20 milliliters, e.g., 1 milliliter, 2 milliliters, 4 milliliters, 5 milliliters, 6 milliliters, 7 milliliters, 8 milliters, 9 milliliters, 10 milliliters, 11 milliliters, 12 milliliters, 13 milliliters, 14 milliliters, 15 milliliters, 16 milliliters, 17 milliliters, 18 milliliters, 19 milliliters, or 20 milliliters, of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μgh/mL In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μg h/mL.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 159 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 231 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 160 μg h/mL and 230 μg h/mL.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 179 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 221 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 180 μg h/mL and 220 μg h/mL.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 189 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 211 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 190 μg h/mL and 210 μgh/mL.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) increasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is less than 149 μgh/mL;

(b) decreasing the initial dose of the oral suspension if the plasma concentration of 5-[[4-[2-[5-(1-hydroxyethyl)

pyridin-2-yl]ethoxy]phenyl]methyl]-1,3-thiazolidine-2,4-dione in the patient is more than 241 μgh/mL; or (c) not changing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is between 150 μgh/mL and 240 μg h/mL;

wherein the increased, decreased, or unchanged dose of the oral suspension is administered to the patient once per day for at least five days.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) increasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is less than 159 μg h/mL;

(b) decreasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 231 μg h/mL; or (c) not changing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is between 160 μg h/mL and 230 μg h/mL;

wherein the increased, decreased, or unchanged dose of the oral suspension is administered to the patient once per day for at least five days.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) increasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is less than 179 μg h/mL;

(b) decreasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 221 μg h/mL; or (c) not changing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is between 180 μg h/mL and 220 μg h/mL;

wherein the increased, decreased, or unchanged dose of the oral suspension is administered to the patient once per day for at least five days.

In another embodiment, the present disclosure provides a method of administering a therapeutically effective amount of 5-[[4-[2-[5-(1-hydroxyethyl)pyridin-2-yl]ethoxy]phenyl]methyl]-1,3-thiazolidine-2,4-dione to a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) increasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is less than 189 μg h/mL;

(b) decreasing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 211 μg h/mL; or (c) not changing the initial dose of the oral suspension if the plasma concentration of 5-[[4-[2-[5-(1-hydroxyethyl)pyridin-2-yl]ethoxy]phenyl]methyl]-1,3-thiazolidine-2,4-dione in the patient is between 190 μg h/mL and 210 μg h/mL;

wherein the increased, decreased, or unchanged dose of the oral suspension is administered to the patient once per day for at least five days.

In another embodiment, the present disclosure provides a method, comprising administering 5-[[4-[2-[5-(1-hydroxyethyl)pyridin-2-yl]ethoxy]phenyl]methyl]-1,3-thiazolidine-2,4-dione to a patient in need thereof, wherein:

(a) an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per mL is administered to the patient once per day for 5 days or more;

(b) the initial dose of the oral suspension is increased if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(c) the initial dose of the oral suspension is decreased the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (d) the initial dose of the oral suspension is unchanged if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μg h/mL; and (e) the increased, decreased, or unchanged dose of the oral suspension is administered to the patient once per day for 5 days or more.

In another embodiment, the present disclosure provides a method, comprising administering 5-[[4-[2-[5-(1-hydroxyethyl)pyridin-2-yl]ethoxy]phenyl]methyl]-1,3-thiazolidine-2,4-dione to a patient in need thereof, wherein:

(a) an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per mL is administered to the patient once per day for 5 days or more;

(b) the initial dose of the oral suspension is increased if the plasma concentration of 5-[[4-[2-[5-(1-hydroxyethyl)pyridin-2-yl]ethoxy]phenyl]methyl]-1,3-thiazolidine-2,4-dione in the patient is less than 159 μg h/mL;

(c) the initial dose of the oral suspension is decreased the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 231 μg h/mL; or (d) the initial dose of the oral suspension is unchanged if the plasma concentration of 5-[[4-[2-[5-(1-hydroxyethyl)pyridin-2-yl]ethoxy]phenyl]methyl]-1,3-thiazolidine-2,4-dione in the patient is between 160 μg h/mL and 230 μg h/mL; and (e) the increased, decreased, or unchanged dose of the oral suspension is administered to the patient once per day for 5 days or more.

In another embodiment, the present disclosure provides a method, comprising administering 5-[[4-[2-[5-(1-hydroxyethyl)pyridin-2-yl]ethoxy]phenyl]methyl]-1,3-thiazolidine-2,4-dione to a patient in need thereof, wherein:

(a) an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per mL is administered to the patient once per day for 5 days or more;

(b) the initial dose of the oral suspension is increased if the plasma concentration of 5-[[4-[2-[5-(1-hydroxyethyl)pyridin-2-yl]ethoxy]phenyl]methyl]-1,3-thiazolidine-2,4-dione in the patient is less than 179 μgh/mL;

(c) the initial dose of the oral suspension is decreased the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 221 μg h/mL; or (d) the initial dose of the oral suspension is unchanged if the plasma concentration of 5-[[4-[2-[5-(1-hydroxyethyl)pyridin-2-yl]ethoxy]phenyl]methyl]-1,3-thiazolidine-2,4-dione in the patient is between 180 μg h/mL and 220 μg h/mL; and (e) the increased, decreased, or unchanged dose of the oral suspension is administered to the patient once per day for 5 days or more.

In another embodiment, the present disclosure provides a method, comprising administering 5-[[4-[2-[5-(1-hydroxyethyl)pyridin-2-yl]ethoxy]phenyl]methyl]-1,3-thiazolidine-2,4-dione to a patient in need thereof, wherein:

(a) an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per mL is administered to the patient once per day for 5 days or more;

(b) the initial dose of the oral suspension is increased if the plasma concentration of 5-[[4-[2-[5-(1-hydroxyethyl)pyridin-2-yl]ethoxy]phenyl]methyl]-1,3-thiazolidine-2,4-dione in the patient is less than 189 μg h/mL;

(c) the initial dose of the oral suspension is decreased the oral suspension if the plasma concentration of 5-[[4-[2-[5-(1-hydroxyethyl)pyridin-2-yl]ethoxy]phenyl]methyl]-1,3-thiazolidine-2,4-dione in the patient is more than 211 μg h/mL; or (d) the initial dose of the oral suspension is unchanged if the plasma concentration of 5-[[4-[2-[5-(1-hydroxyethyl)pyridin-2-yl]ethoxy]phenyl]methyl]-1,3-thiazolidine-2,4-dione in the patient is between 190 μg h/mL and 210 μg h/mL; and (e) the increased, decreased, or unchanged dose of the oral suspension is administered to the patient once per day for 5 days or more.

In another embodiment, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 149 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 241 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 150 μg h/mL and 240 μgh/mL.

In another embodiment, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 159 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 231 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 160 μg h/mL and 230 μgh/mL.

In another embodiment, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 159 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 231 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 160 μg h/mL and 230 μg h/mL.

In another embodiment, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 179 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 221 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 180 μg h/mL and 220 μgh/mL.

In another embodiment, the present disclosure provides a method of treating a disease or disorder in a patient in need thereof, the method comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is less than 189 μg h/mL;

(b) administering a lower dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is more than 211 μg h/mL; or (c) administering an unchanged dose of the oral suspension to the patient once per day if the plasma concentration of 5-[[4-[2-[5-(1-hydroxyethyl)pyridin-2-yl]ethoxy]phenyl]methyl]-1,3-thiazolidine-2,4-dione in the patient is between 190 μg h/mL and 210 μgh/mL.

In some embodiments of the present disclosure, the methods further comprise determining the plasma concentration of 5-[[4-[2-[5-(1-hydroxyethyl)pyridin-2-yl]ethoxy]phenyl]methyl]-1,3-thiazolidine-2,4-dione in the patient, e.g., after administering an initial dose of Compound (1), e.g., as an oral suspension, to the patient once per day for at least 5 days.

The disclosure also provides the following particular embodiments relating to methods of treating a disease or disorder in a patient in need thereof.

Embodiment IA. A method of treating a disease or disorder in a patient in need thereof, the method comprising administering Compound (1), or a pharmaceutically acceptable salt thereof, to the patient, wherein the patient achieves a Compound (1) plasma $AUC_{ss}$ of about 50 μgh/mL to about 300 μgh/mL after at least five days of orally administering Compound (1), or a pharmaceutically acceptable salt thereof, to the patient per day.

Embodiment I.A method of treating a disease or disorder in a patient in need thereof, the method comprising administering Compound (1), or a pharmaceutically acceptable salt thereof, to the patient, wherein the patient achieves a Compound (1) plasma $AUC_{ss}$ of about 100 μg h/mL to about 300 μg h/mL after at least five days of orally administering Compound (1), or a pharmaceutically acceptable salt thereof, to the patient per day.

Embodiment II. The method of Embodiment I, wherein the patient achieves a Compound (1) plasma $AUC_{ss}$ of about 150 μg h/mL to about 250 μg h/mL.

Embodiment III. The method of Embodiment II, wherein the patient achieves a Compound (1) plasma $AUC_{ss}$ of about 175 μg h/mL to about 225 μg h/mL.

Embodiment IV. The method of Embodiment III, wherein the patient achieves a Compound (1) plasma $AUC_{ss}$ of about 200 μg h/mL.

Embodiment V. A method of treating a disease or disorder in a patient in need thereof, the method comprising administering Compound (1), or a pharmaceutically acceptable salt thereof, to the patient, wherein the patient achieves a Compound (1) plasma $C_{min\ ss}$ of about 2306 ng/mL to about 9126 ng/mL after at least five days orally administering Compound (1), or a pharmaceutically acceptable salt thereof, to the patient per day.

Embodiment VI. The method of Embodiment V, wherein the patient achieves a Compound (1) plasma $C_{min\ ss}$ of about 4011 ng/mL to about 7421 ng/mL.

Embodiment VII. The method of Embodiment VI, wherein the patient achieves a Compound (1) plasma $C_{min\ ss}$ of about 4864 ng/mL to about 6569 ng/mL.

Embodiment VIII. The method of Embodiment VII, wherein the patient achieves a Compound (1) plasma $C_{min\ ss}$ of about 5716 ng/mL.

Embodiment IX. The method of any one of Embodiments I-VIII, wherein the disease or disorder is selected from the group consisting of central nervous system disease or disorder, mitochondrial disease, nonalcoholic steatohepatitis (NASH), nonalcoholic fatty liver disease (NAFLD), chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

Embodiment X. The method of Embodiment IX, wherein the disease or disorder is a central nervous system disease or disorder.

Embodiment XI. The method of Embodiment X, wherein the central nervous system disease or disorder is selected from the group consisting of neurodegenerative disease, cerebrovascular disease, seizure, epilepsy, viral disease, neuroinflammatory disease, brain tumor, organic acidemias, fatty acid disorder, and genetic mitochondrial disorder.

Embodiment XII. The method of Embodiment XI, wherein the central nervous system disease or disorder is a neurodegenerative disease.

Embodiment XIII. The method of Embodiment XII, wherein the neurodegenerative disease is selected from the group consisting of Alzheimer's disease, Huntington's chorea, Parkinson's disease, multiple sclerosis, leukodystrophy, ALS, degenerative ataxia, multiple system atrophy, and a motor neuron disease.

Embodiment XIV. The method of Embodiment XIII, wherein the leukodystrophy is X-linked adrenoleukodystrophy.

Embodiment XV. The method of Embodiment XIII, wherein the degenerative ataxia is Friedreich's ataxia.

Embodiment XVI. The method of Embodiment XIII, wherein the motor neuron disease is selected from the group consisting of progressive bulbar palsy, pseudobulbar palsy, primary lateral sclerosis (PLS), progressive muscular atrophy, spinal muscular atrophy (SMA), post-polio syndrome (PPS)-Marie-Tooth disease, Guillan-Barré syndrome, and adrenomyeloneuropathy (AMN).

Embodiment XVII. The method of Embodiment IX, wherein the central nervous system disorder is a cerebrovascular disease selected from the group consisting of global or local ischemia, intracerebral haemorrhage, stroke, and vascular dementia.

Embodiment XVIII. The method of Embodiment IX, the central nervous system disorder is a viral disease selected from the group consisting of meningitis, encephalitis, rabies, measles, mumps, poliomyelitis, herpes simplex, and varicella zoster.

Embodiment XIX. The method of Embodiment IX, wherein the rare metabolic disease is selected from the group consisting of organic acidemias, fatty acid disorders and genetic mitochondrial disorders.

Embodiment XX. The method of Embodiment IX, wherein the disease or disorder is a mitochondrial disease.

Embodiment XXI. The method of Embodiment XX, wherein the mitochondrial disease is a primary mitochondrial disorder selected from the group consisting of Rett syndrome, Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX definient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

Embodiment XXII. The method of Embodiment XX, wherein the mitochondrial disease is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

Embodiment XXIII. The method of Embodiment XX, wherein the mitochondrial disease is a secondary mitochondrial disorder selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy and Bethlem myopathy); DiGeorge syndrome; and neuromuscular disorders (such as limb-girdle muscular dystrophy, inflammatory myopathies, Charcot Marie Tooth (CMT) neuropathy, and drug-induced peripheral neuropathies).

Embodiment XXIV. The method of Embodiment IX, wherein the disease or disorder is nonalcoholic steatohepatitis (NASH).

Embodiment XXV. The method of any one of Embodiments I-XXIV, wherein Compound (1) HCl is administered to the patient.

Embodiment XXVI. The method of Embodiment XXV, wherein the Compound (1) HCl is administered to the patient as a suspension comprising about 15 mg of Compound (1) HCl per mL. In another embodiment, the Compound (1) HCl is administered to the patient as a tablet, capsule, or other solid form comprising about 30 mg of Compound (1) HCl, about 60 mg of Compound (1) HCl, or about 90 mg of Compound (1) HCl.

The disclosure also provides the following particular embodiments relating to Compound (1), or a pharmaceutically acceptable salt thereof, for use in treating a disease or disorder, or for administering a therapeutically effective amount of this drug.

Embodiment 1. Compound (1), or a pharmaceutically acceptable salt thereof, for use in treating a disease or disorder in a patient, wherein:

(i) the $AUC_{ss}$ of Compound (1) in plasma from the patient is about 34 μg h/mL to about 300 μg h/mL;

(ii) the $C_{min\ ss}$ of Compound (1) in plasma from the patient is about 55 ng/mL to about 9126 ng/mL; or (iii) the $AUC_{ss}$ of Compound (1) in plasma from the patient is about 34 μg h/mL to about 300 μg h/mL, and the $C_{min\ ss}$ of Compound (1) in plasma from the patient is about 55 ng/mL to about 9126 ng/mL; and the $AUC_{ss}$ of (i), the $C_{min\ ss}$ of (ii), or the $AUC_{ss}$ and $C_{min\ ss}$ of (iii) is measured after at least five days of orally administering Compound (1), or a pharmaceutically acceptable salt thereof, to the patient per day.

Embodiment 2. The Compound (1), or a pharmaceutically acceptable salt thereof, for use of Embodiment 1, wherein the $AUC_{ss}$ of Compound (1) is about 100 μg h/mL to about 300 μg h/mL.

Embodiment 3. The Compound (1), or a pharmaceutically acceptable salt thereof, for use of Embodiment 2, wherein the $AUC_{ss}$ of Compound (1) is about 150 μg h/mL to about 250 μg h/mL.

Embodiment 4. The Compound (1), or a pharmaceutically acceptable salt thereof, for use of Embodiment 3, wherein the $AUC_{ss}$ of Compound (1) is about 175 μg h/mL to about 225 μg h/mL.

Embodiment 5. The Compound (1), or a pharmaceutically acceptable salt thereof, for use of Embodiment 5, wherein the $AUC_{ss}$ of Compound (1) is about 200 μg h/mL.

Embodiment 6. The Compound (1), or a pharmaceutically acceptable salt thereof, for use of any one of Embodiments 1-5, wherein the $C_{min\ ss}$ of Compound (1) is about 2306 ng/mL to about 9126 ng/mL.

Embodiment 7. The Compound (1), or a pharmaceutically acceptable salt thereof, for use of any one of Embodiment 1-6, wherein the $C_{min\ ss}$ of Compound (1) is about 4011 ng/mL to about 7421 ng/mL.

Embodiment 8. The Compound (1), or a pharmaceutically acceptable salt thereof, for use of any one of Embodiment 1-7, wherein the $C_{min\ ss}$ of Compound (1) is about 4864 ng/mL to about 6569 ng/mL.

Embodiment 9. The Compound (1), or a pharmaceutically acceptable salt thereof, for use of any one of Embodiment 1-8, wherein the $C_{min\ ss}$ of Compound (1) is about 5716 ng/mL.

Embodiment 10. The Compound (1), or a pharmaceutically acceptable salt thereof, for use of any one of Embodiment 1-9, wherein the $AUC_{ss}$, $C_{min\ ss}$, or $AUC_{ss}$ and $C_{min\ ss}$ is measured after at least seven days.

Embodiment 11. The Compound (1), or a pharmaceutically acceptable salt thereof, for use of Embodiment 10, wherein the $AUC_{ss}$, $C_{min\ ss}$, or $AUC_{ss}$ and $C_{min\ ss}$ is measured after at least ten days.

Embodiment 12. The Compound (1), or a pharmaceutically acceptable salt thereof, for use of Embodiment 11, wherein the $AUC_{ss}$, $C_{min\ ss}$, or $AUC_{ss}$ and $C_{min\ ss}$ is measured after at least fourteen days.

Embodiment 13. The Compound (1), or a pharmaceutically acceptable salt thereof, for use of any one of Embodiment 1-12, wherein Compound (1) HCl is administered to the patient in need thereof.

Embodiment 14. The Compound (1) HCl for use of Embodiment 13, wherein the Compound (1) HCl is administered to the patient as a suspension comprising about 15 mg of Compound (1) HCl per mL. In another embodiment, the Compound (1) HCl is administered to the patient as a tablet, capsule, or other solid form comprising about 30 mg of Compound (1) HCl, about 60 mg of Compound (1) HCl, or about 90 mg of Compound (1) HCl.

Embodiment 15. Compound (1), or a pharmaceutically acceptable salt thereof, for use in administering a therapeutically effective amount of Compound (1) to a patient in need thereof, wherein:

(a) an amount of Compound (1), or a pharmaceutically acceptable salt thereof, is administered to the patient per day;

(b) a plasma sample is obtained from the patient after at least 5 days of administration according to (a);

(c) the plasma concentration of Compound (1) in the plasma sample obtained in (b) is determined; and (d) a recalculated amount of Compound (1), or a pharmaceutically acceptable salt thereof, in milligrams, is administered to the patient per day as determined according to the Equation 1:

$$\text{new amount in mg} = SD \times \left(\frac{CMT}{PC}\right), \qquad \text{Equation 1}$$

wherein:

SD is the amount of Compound (1), or a pharmaceutically acceptable salt thereof, administered to the patient in (a) in mg;

CMT is the $C_{min\ target}$ in ng/mL;

$C_{min\ target}$=(target AUC ng h/mL×0.0341±20%)−1104±20%; and

PC is the plasma concentration in ng/mL of Compound (1) determined in (c). In some embodiments, $C_{min\ target}$=(target AUC ng h/mL×0.0341±10%)−1104±10%. In some embodiments, $C_{min\ target}$=(target AUC ng h/mL×0.0341±5%)−1104±5%. In some embodiments, $C_{min\ target}$=(target AUC ng h/mL×0.0341)−1104.

Embodiment 16. The Compound (1), or a pharmaceutically acceptable salt thereof, for use of Embodiment 15, wherein the plasma sample is obtained from the patient after at least 7 days of administering according to (a).

Embodiment 17. The Compound (1), or a pharmaceutically acceptable salt thereof, for use of Embodiment 16, wherein a plasma sample is obtained from the patient after at least 10 days of administering according to (a).

Embodiment 18. The Compound (1), or a pharmaceutically acceptable salt thereof, for use of Embodiment 17, wherein a plasma sample is obtained from the patient after at least 14 days of administering according to (a).

Embodiment 19. The Compound (1), or a pharmaceutically acceptable salt thereof, for use of any one of Embodiments 15-18, wherein the Compound (1), or a pharmaceutically acceptable salt thereof, is administered orally to the patient in (a) and (d).

Embodiment 20. The Compound (1), or a pharmaceutically acceptable salt thereof, for use of any one of Embodiments 15-19, wherein Compound (1) HCl is administered to the patient per day in (a) and (d).

Embodiment 21. The Compound (1) HCl for use of Embodiment 20, wherein about 150 mg of Compound (1) HCl is administered to the patient per day in (a) and the target AUC is about 200 μg h/mL.

Embodiment 22. The 5-[[4-[2-[5-(1-hydroxyethyl)pyridin-2-yl]ethoxy]phenyl]methyl]-1,3-thiazolidine-2,4-dionehydrochloride for use of Embodiments 20 or 21, wherein a recalculated amount of Compound (1) HCl is administered to the patient per day in (d).

Embodiment 23. The Compound (1) HCl for use of any one of Embodiments 20-22, wherein the Compound (1) HCl is administered to the patient in (i) and (iv) as a suspension comprising about 15 mg of Compound (1) HCl per mL. In another embodiment, the Compound (1) HCl is administered to the patient in (i) and (iv) as a tablet, capsule, or other solid form comprising about 30 mg of Compound (1) HCl, about 60 mg of Compound (1) HCl, or about 90 mg of Compound (1) HCl Embodiment 24. The 5-[[4-[2-[5-(1-hydroxyethyl)pyridin-2-yl]ethoxy]phenyl]methyl]-1,3-thiazolidine-2,4-dione, or a pharmaceutically acceptable salt thereof, for use of any one of Embodiments 1-23, wherein the patient has a disease or disorder.

Embodiment 25. Compound (1), or a pharmaceutically acceptable salt thereof, for use in treating a disease or disorder in a patient, comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for at least 5 days; and (a) administering a higher dose of the oral suspension to the patient once per day if the plasma concentration of Compound (1) in the patient is less than 149 μg h/mL;

(b) administering a lower dose of the oral suspension to the patient once per day if the plasma concentration of Compound (1) in the patient is more than 241 μg h/mL; or (c) administering an unchanged dose of the oral suspension to the patient once per day if the plasma concentration of 5 Compound (1) in the patient is between 150 μg h/mL and 240 μg h/mL.

Embodiment 26. Compound (1), or a pharmaceutically acceptable salt thereof, for use in treating a disease or disorder in a patient, comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of Compound (1) in the patient is less than 159 µg h/mL;

(b) administering a lower dose of the oral suspension to the patient once per day if the plasma concentration of Compound (1) in the patient is more than 231 µg h/mL; or (c) administering an unchanged dose of the oral suspension to the patient once per day if the plasma concentration of 5 Compound (1) in the patient is between 160 µg h/mL and 230 µg h/mL.

Embodiment 27. Compound (1), or a pharmaceutically acceptable salt thereof, for use in treating a disease or disorder in a patient, comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of Compound (1) in the patient is less than 179 µg h/mL;

(b) administering a lower dose of the oral suspension to the patient once per day if the plasma concentration of Compound (1) in the patient is more than 221 µg h/mL; or (c) administering an unchanged dose of the oral suspension to the patient once per day if the plasma concentration of 5 Compound (1) in the patient is between 180 µg h/mL and 220 µg h/mL.

Embodiment 28. Compound (1), or a pharmaceutically acceptable salt thereof, for use in treating a disease or disorder in a patient, comprising administering an initial dose of 5 to 20 milliliters of an oral suspension comprising 15 mg of 5-[[4-[2-[5-(1-hydroxyethyl)pyridin-2-yl]ethoxy]phenyl]methyl]-1,3-thiazolidine-2,4-dione hydrochloride per ml to the patient once per day for 5 days or more; and (a) administering a higher dose of the oral suspension to the patient once per day if the plasma concentration of Compound (1) in the patient is less than 189 µg h/mL;

(b) administering a lower dose of the oral suspension to the patient once per day if the plasma concentration of Compound (1) in the patient is more than 211 µg h/mL; or (c) administering an unchanged dose of the oral suspension to the patient once per day if the plasma concentration of Compound (1) in the patient is between 190 µg h/mL and 210 µg h/mL.

In another embodiment, the present disclosure provides a method of administering a therapeutically effective amount of Compound (1) to a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 or more days; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to:

(i) Equation 8a:

$$\text{Drecal}=\text{Dinitial}*(\text{AUCTar}/AUC\_0t) \quad \text{Equation 8a}$$

wherein:

$D_{recal}$ is recalculated dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

$D_{initial}$ is the initial dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

$AUC_{Tar}$ is the targeted exposure of Compound (1) in the patient 24 hours after the last administration in (a) in ng h/ml; and AUC_0t is the calculated exposure of Compound (1) in the patient 24 hours after the last administration in (a) in ng h/ml;

(ii) Equation 8b:

$$AUC\_0t=(28.31+0.472*\Delta T)*C+(34410+2234*\Delta T)*D_{initial}/150 \quad \text{Equation 8b}$$

wherein:

AUC_0t is the calculated exposure of Compound (1) in the patient 24 hours after the last administration in (a) in ng h/ml;

$D_{initial}$ is the initial dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

C is the plasma concentration of Compound (1) in the patient in ng/ml, wherein the plasma sample is taken from the patient 24±6 hours after the last administration in (a); and ΔT is the difference between the time the plasma sample is taken from the patient and 24 hours after the last administration in (a) in hours;

wherein the targeted exposure is 50,000 ng h/mL to 250,000 ng h/mL.

For example, with respect to ΔT, if the plasma sample was taken 24.5 hours after the last administration the ΔT would be 0.5 hours. Likewise, if the plasma sample was taken 23 hours after the last administration the ΔT would bel hour.

In another embodiment, the present disclosure provides a method of administering a therapeutically effective amount of Compound (1) to a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 days or more; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to Equations 8a and 8b, wherein the targeted exposure is 100,000 ng h/mL to 200,000 ng h/mL.

In another embodiment, the present disclosure provides a method of administering a therapeutically effective amount of Compound (1) to a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 days or more; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to Equations 8a and 8b, wherein the targeted exposure is 100,000 ng h/mL, 120,000 ng h/mL, 130,000 ng h/mL, 140,000 ng h/mL, 150,000 ng h/mL, 160,000 ng h/mL, 175,000 ng h/mL, 180,000 ng h/mL, 190,000 ng h/mL, or 200,000 ng h/mL.

In another embodiment, the present disclosure provides a method treating a disease or disorder in a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 days or more; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to Equations 8a and 8b, wherein the targeted exposure is 50,000 ng h/mL to 250,000 ng h/mL.

In another embodiment, the present disclosure provides a method treating a disease or disorder in a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 days or more; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to Equations 8a and 8b, wherein the targeted exposure is 100,000 ng h/mL to 200,000 ng h/mL.

In another embodiment, the present disclosure provides a method treating a disease or disorder in a patient in need thereof, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 days or more; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to Equations 8a and 8b, wherein the targeted exposure is 100,000 ng h/mL, 120,000 ng h/mL, 130,000 ng h/mL, 140,000 ng h/mL, 150,000 ng h/mL, 160,000 ng h/mL, 175,000 ng h/mL, 180,000 ng h/mL, 190,000 ng h/mL, or 200,000 ng h/mL.

III. Diseases and Disorders

The methods and uses of the present disclosure comprise administering Compound (1), or a pharmaceutically acceptable salt thereof, to a patient in need thereof, to treat a variety of diseases or disorders.

In one embodiment, the disease or disorder is regulated by peroxisome proliferator-activated receptor gamma (PPAR-γ). PPAR-γ regulates, inter alia, fatty acid storage and glucose metabolism, and has been implicated in the pathology of numerous diseases and disorders.

In another embodiment, the disease or disorder is selected from the group consisting of central nervous system disease or disorder, mitochondrial disease, nonalcoholic steatohepatitis (NASH), nonalcoholic fatty liver disease (NAFLD), chronic granulomatous disorder, a polycystic ovary syndrome, a thyroid carcinoma, a thyroid autoimmune disorder, a pituitary adenoma, atherosclerosis, hypertension, a skin disease, an inflammation and autoimmune disease, and an inflammatory respiratory disease.

In another embodiment, the disease or disorder is a central nervous system disease or disorder.

In another embodiment, the disease or disorder is selected from the group consisting of neurodegenerative disease, cerebrovascular disease, seizure, epilepsy, viral disease, neuroinflammatory disease, brain tumor, organic acidemias, fatty acid disorder, and genetic mitochondrial disorder.

In another embodiment, the disease or disorder is a neurodegenerative disease.

In another embodiment, the disease or disorder is selected from the group consisting of Alzheimer's disease, Huntington's chorea, Parkinson's disease, multiple sclerosis, leukodystrophy, ALS, degenerative ataxia, multiple system atrophy, and a motor neuron disease.

In another embodiment, the disease or disorder is selected from the group consisting of Alzheimer's disease, Huntington's chorea, Parkinson's disease, multiple sclerosis, neuromyelitis optica, leukodystrophy, ALS, degenerative ataxia, multiple system atrophy, NBIA (neurodegeneration and brain iron accumulation disorders), neuromyopathy, and a motor neuron disease.

In another embodiment, the disease or disorder is X-linked adrenoleukodystrophy.

In another embodiment, the disease or disorder is degenerative ataxia. In another embodiment, the degenerative ataxia is Friedreich's ataxia.

In another embodiment, the disease or disorder is a motor neuron disease.

In another embodiment, the motor neuron disease is selected from the group consisting of progressive bulbar palsy, pseudobulbar palsy, primary lateral sclerosis (PLS), progressive muscular atrophy, spinal muscular atrophy (SMA), post-polio syndrome (PPS)-Marie-Tooth disease, Guillan-Barré syndrome, and adrenomyeloneuropathy (AMN).

In another embodiment, the disease or disorder is a central nervous system disorder. In another embodiment, the central nervous system disorder is acerebrovascular disease selected from the group consisting of global or local ischemia, intracerebral haemorrhage, stroke, and vascular dementia. In another embodiment, the central nervous system disorder is a viral disease selected from the group consisting of meningitis, encephalitis, rabies, measles, mumps, poliomyelitis, herpes simplex, and varicella zoster.

In another embodiment, the disease or disorder is a rare metabolic disease. In another embodiment, the rare metabolic disease is selected from the group consisting of organic acidemias, fatty acid disorders and genetic mitochondrial disorders.

In another embodiment, the disease or disorder is a mitochondrial disease.

Mitochondria are tiny subunits present inside every cell of the human body except red blood cells. Mitochondria's main role is to transform food an oxygen that enter the cells into useful energy. Pyruvate uptake across the mitochondrial inner membrane is a central branch point in cellular energy metabolism with the ability to balance glycolysis and oxidative phosphorylation and poise catabolic an anabolic metabolism. (See, e.g., Divakaruni et al., *PNAS* 110(14): 5422-5427 (2013)). The mitochondrial pyruvate carrier (MPC) is an inner-membrane transporter that facilitates pyruvate uptake from the cytoplasm to mitochondria. It is a central regulator of mitochondrial substrate utilization, and restrictions in mitochondrial pyruvate uptake can potentiate the use of fatty acids and a range of amino acids to fuel cellular energetics and biosynthesis. (See, e.g., Divakaruni et al., *J. Cell Biol.* (2017)).

The MPC contains two proteins, MPC1 and MPC2, that form a carrier complex in the inner mitochondrial membrane. MPC transports pyruvate into mitochondrial matrix that is required for pyruvate metabolism and is critical for metabolic pathways. (See, e.g., McCommis et al., *Biochem. J.* 466: 443-454 (2015)).

Mitochondrial diseases are a group of disorders, each of which involves a mitochondrial dysfunction. Mitochondrial diseases are chronic, genetic, and often inherited disorders that that occur when mitochondria fail to produce enough energy for the body to function properly. Mitochondrial diseases can be present at birth, but can also occur at any age. These diseases can affect the cells of the brain, nerves, muscles, kidneys, heart, liver, eyes, ears, and/or pancreas. Mitochondrial dysfunction occurs when the mitochondria do not work as well as they should due to another disease or condition. Mitochondrial disease refers to a heterogeneous group of disorders that include primary and secondary mitochondrial disorders (See e.g., Niyazov et al., *Mol. Syndromol.* 7:122-137 (2016)). Primary mitochondrial disorders can be due to germline mutations in mitochondrial DNA (mtDNA) and/or nuclear DNA (nDNA) genes either encoding OXPHOS (oxidative phosphorylation) proteins directly or they affect OXPHOS function by impacting production of the complex machinery needed to run the OXPHOS process. Secondary mitochondrial disorders by contrast occur in many pathologic processes not involving OXPHOS, including inherited diseases with germline mutations in non-OXPHOS genes. Secondary mitochondrial disorders can also be acquired secondary to adverse environmental effects which can cause oxidative stress. Many conditions can lead to secondary mitochondrial dysfunction including autism, Parkinson's disease, Alzheimer's disease, muscular dystrophy, Lou Gehrig's disease, diabetes and cancer.

In another embodiment, the mitochondrial disease is a primary mitochondrial disorder selected from the group consisting of Rett syndrome, Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX definient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxy-acetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

In another embodiment, the mitochondrial disease is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

In another embodiment, the mitochondrial disease is a secondary mitochondrial disorder selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy, Bethlem myopathy, oculopharyngeal distal and Emery-Dreifuss); DiGeorge syndrome; and neuromuscular disorders (such as limb-girdle muscular dystrophy, inflammatory myopathies, Charcot Marie Tooth (CMT) neuropathy, and drug-induced peripheral neuropathies).

In another embodiment, the disease or disorder is nonalcoholic steatohepatitis (NASH).

IV. Pharmaceutical Compositions and Use as a Medicament

Pharmaceutical compositions comprising Compound (I), or a pharmaceutically acceptable salt thereof, and a pharmaceutically acceptable excipient, can be administered by any suitable route of administration. For example, any of oral, intraoral, topical, epicutaneous, subcutaneous, transdermal, intramuscular, parenteral, ocular, rectal, vaginal, inhalation, buccal, sublingual and intranasal delivery routes can be suitable.

The present disclosure also provides the use of a compound of Compound (1), or a pharmaceutically acceptable salt thereof, in the manufacture of a medicament for the treating a disease or disorder in a patient in need thereof.

In one embodiment, Compound (I), or a pharmaceutically acceptable salt thereof, is administered orally. Oral forms of pharmaceutical compositions can be solid or liquid. Suitable oral dosage forms include tablets, capsules, pills, granules, suspensions, emulsions, syrups or solutions. The pharmaceutical compositions may be a solid form selected from, e.g., tablets, capsules, pills, or granules. In an embodiment, the oral form is a tablet. In another embodiment, the oral form is an oral solution or suspension. These are advantageous when the patient has difficulty swallowing, for example as a result of the disease or for geriatric and pediatric use. Sublingual preparations are also advantageous.

The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Thus, the dose of the active agent will depend on the nature and degree of the condition, the age and condition of the patient, and other factors known to those skilled in the art. A typical daily dosage is from 0.1 to 200 mg, such as from 20 to 200 mg, e.g., for an adult 10-100 mg given as a single dose with no further dosing or in multiple doses, for example one to three times per day. The compounds described herein may also be administered in daily doses of from 80 to 600 mg. In one embodiment, the daily dose for an adult is from about 50 mg to about 300 mg. In one embodiment, the daily dose for an adult is about 90 mg, 120 mg, 150 mg, 180 mg, or about 210 mg. A daily dose for a child is from about 0.1 to about 200 mg. In another embodiment, the daily for a child is from about 10 mg to about 100 mg.

The pharmaceutical compositions may contain conventional excipients known in the art and may be prepared by conventional methods. A specific compound or mixture of compounds may be selected for a particular route of delivery. Some compounds or mixtures of compounds may also be suitable based on their use to treat NAFLD and NASH, X-ALD, or other diseases or disorder Oral dosage forms may be prepared by combining Compound (I), or a pharmaceutically acceptable salt thereof, in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, stabilizers, and disintegrating agents.

Due to their ease of administration, tablets, caplets, and capsules (such as hard gelatin, HPMC, or starch capsules) represent an embodiment of the solid oral dosage unit forms, in which case solid pharmaceutical excipients are used. If desired, tablets or caplets can be coated by standard aqueous or nonaqueous techniques. These dosage forms can be prepared by any of the methods of pharmacy. In general, pharmaceutical compositions and dosage forms are prepared by uniformly and intimately admixing one or more Compounds of the Disclosure with liquid carriers, finely divided solid carriers, or both, and then shaping the product into the desired presentation if necessary.

For example, a tablet can be prepared by compression or molding. Compressed tablets can be prepared by compressing in a suitable machine one or more Compound (I), or a pharmaceutically acceptable salt thereof, in a free-flowing form, such as a powder or granules, optionally mixed with one or more excipients. Molded tablets can be made by molding in a suitable machine a mixture of the powdered compound moistened with an inert liquid diluent.

The pharmaceutical compositions may further comprise one or more other therapeutic agents. Combination treatments may be administered simultaneously, sequentially, or separately, by the same or by different routes, or before, during, and after surgical or intervention procedures.

In one embodiment, the present disclosure provides a pharmaceutical composition comprising Compound (1) HCl as an aqueous suspension.

In another embodiment, the present disclosure provides a pharmaceutical composition comprising Compound (1) HCl, Polysorbate 80, carboxymethylcellulose sodium, and water.

In another embodiment, the present disclosure provides a pharmaceutical composition comprising Compound (1) HCl, colloidal microcrystalline cellulose, and carboxymethylcellulose sodium.

The pharmaceutical compositions of the present disclosure comprising Compound (1) HCl may also, optionally, comprise sweeting agents, e.g., sorbitol powder, saccharin sodium, preservatives, e.g., sodium benzoate, flavorings, pH regulators, e.g., sodium citrate, citric acid monohydrate.

Compound (I), or a pharmaceutically acceptable salt thereof, can be used according to the disclosure when the patient is also administered or in combination with one or more of another therapeutic agent selected from antiinflammatory and analgesic agents, antidiabetics (e.g., metformin), dopamine agonists (e.g. levodopa), MAO-B inhibitors, catechol O-methyltransferase (COMT) inhibitors, anticholinergics, other antiparkinsonians (e.g. amantadine), anti-NMDA receptors (e.g. memantine), cholinesterase inhibitors, ACE inhibitors, glutamate antagonist (e.g. riluzole), antioxidants, immunomodulators (e.g. fingolimod, anti CD52, CD25 and CD20 monoclonal antibodies, interferon-β-1a, natalizumab, laquinimod, dimethylfumarate) chemotherapeutics, enzyme replacement therapy agents, substrate reduction therapy agents, corticosteroids, antiproliferatives (e.g. methotrexate), anticonvulsant medications, anticoagulants, antihypertensives and neuroprotectives. The compounds of the disclosure may also be used when the patient is undergoing gene therapy, bone marrow transplantation, deep brain stimulation or radiotherapy.

The one or more therapeutic agents include a sulfonylurea (e.g., glimepiride, glipizide, glyburide), a glinidine (also known as meglitinides), a thiazolidinedione (e.g., pioglitazone, rosiglitazone, lobeglitazone), a dipeptidyl peptidase 4 (DPP4) inhibitor (e.g., sitagliptin, vildagliptin, saxagliptin, linagliptin, gemigliptin, anagliptin, teneligliptin, alogliptin, trelagliptin, dutogliptin, omarigliptin), a sodium/glucose cotransporter 2 (SGLT2) inhibitor (e.g., canagliflozin, dapagliflozin), a glucagon-like peptide-1 (GLP1) receptor agonist (e.g., exenatide, liraglutide, lixisenatide, albiglutide, dulaglutide, taspoglutide, semaglutide), glucagon like peptide-1 (GLP-1), and insulin (e.g., animal insulin preparations extracted from the pancreas of cattle or pigs; human insulin preparations synthesized by genetic engineering using *Escherichia coli* or yeast; insulin zinc; protamine insulin zinc; insulin fragments or derivatives (e.g., INS-1), and oral insulin preparations.

V. Definitions

Various examples and embodiments of the inventive subject matter disclosed here are possible and will be apparent to a person of ordinary skill in the art, given the benefit of this disclosure. In this disclosure reference to "some embodiments," "certain embodiments," "certain exemplary embodiments," "particular embodiments," and similar phrases each means that those embodiments are non-limiting examples of the inventive subject matter, and there are alternative embodiments which are not excluded.

The articles "a," "an," and "the" are used herein to refer to one or to more than one (i.e., to at least one) of the grammatical object of the article. By way of example, "an element" means one element or more than one element.

The term "about," as used herein, includes the recited number±10%. Thus, "about 10" means 9 to 11.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also contemplated and within the scope of this disclosure.

The term "ameliorate" in the context of this present disclosure is understood as meaning any improvement on the situation of the patient treated.

The term "bid administration" or "BID" means twice daily administration of a therapeutic.

The term "SAD" means a single oral dose administration of a therapeutic.

By an "effective" amount or a "therapeutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The term "treatment" or "to treat" and similar terms in the context of this specification means to ameliorate or eliminate the disease or one or more symptoms associated with said disease. "Treatment" also encompasses ameliorating or eliminating the physiological sequelae of the disease.

The term "pharmaceutically acceptable salt" refers to salts prepared from pharmaceutically acceptable inorganic and organic acids.

The term "prevention" or "to prevent" refers to the reduction in the risk of acquiring or developing a given disease or disorder, or the reduction or inhibition of the recurrence or a disease or disorder.

As used herein, the phrase "PK variability" or "pharmacokinetic variability" refer to inter-individual variations of a drugs pharmacokinetic parameters, resulting in different plasma concentration-time profiles after administration of the same dose to different patients.

As used herein, the term "steady-state" refers to the pharmacokinetic situation when the rate of drug administration is equal to the rate of drug elimination.

As used herein, the terms "AUC at steady-state" or "$AUC_{ss}$" refer to the overall amount of drug in plasma at steady-state.

As used herein, the terms "trough value at steady state" or "$C_{min\ ss}$" refer to minimum steady-state plasma drug concentration during a dosage interval.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The term "primary mitochondrial disorder" or "PMD" refers to a mitochondrial disease that can occur due to germline mutations in mitochondrial DNA (mtDNA) and/or nuclear DNA (nDNA) genes encoding the electron transport chain (ETC) proteins and therefore the production of adenosine-triphosphate (ΔTP), the major cellular energy carrier.

The term "secondary mitochondrial disorder" or "SMD" refers to a mitochondrial disease accompanying many pathologic processes not involving oxidative phosphorylation (OXPHOS), including inherited diseases with germline mutations in non-OXPHOS genes. SMD can also be acquired secondary to adverse environmental effects which can cause oxidative stress.

EXAMPLES

The methods of treatment or prevention and uses described herein are now further detailed with reference to the following example. These examples are provided for the purpose of illustration only and the embodiments described herein should in no way be construed as being limited to these examples. Rather, the embodiments should be construed to encompass any and all variations which become evident as a result of the teaching provided herein.

Example 1

Data from a multiple ascending dose (MAD) study of Compound (1) HCl in human subjects at 135 mg and 270 mg confirmed that there was no change in clearance with time. The mean $AUC_{0\text{-}tau\ ss}$ (% CV) (135 μg·h/mL (20)) and $Cmax_{ss}$ (% CV) (9488 ng/ml (17)) was determined at the steady state day 8 in case 135 mgs. The mean $AUC_{0\text{-}tau\ ss}$ (% CV) (299 μg·h/mL (21) and $Cmax_{ss}$(% CV) (17200 ng/ml (18) was determined at the steady state day 8 in case 270 mgrs.

The day 8 data from the MAD study showed that $C_{min\ ss}$ and $AUC_{0\text{-}tau\ ss}$ were correlated as shown in FIG. 1. The equation describing the line of best fit indicates that the $C_{min\ ss}$ associated with the target $AUC_{0\text{-}tau\ ss}$ (200 μg·h/mL) for effect is 5716 ng/mL.

Across all ascending dose studies in humans the increase in dose is linearly related to the increase in AUC. Because of the inter subject variability in clearance it is required to select a start dose which is not excessively above the 200 μg·h/mL target $AUC_{ss}$.

The PK data from the MAD study was used to generate a start dose which is most likely no cause toxicity or adverse events in subjects. A dose of 150 mg was chosen as it would give a geometric mean AUCtau of 167 μg·h/mL SD 33 with a 95% confidence interval of 102-232 μg·h/mL. At this dose approximated 75% of patients will be below 200 μg·h/mL and it is unlikely that any patient will exceed 240 μg·h/mL.

After 2 weeks of dosing a $C_{min\ ss}$ PK sample will be collected from each patient and the result will be used to adjust the dose of Compound (1) HCl using Equation 3:

$$\text{new amount in mg} = 150\times\left(\frac{5716}{PC}\right), \quad \text{Equation 23}$$

wherein PC is the plasma concentration in ng/mL of 5-[[4-[2-[5-(1-hydroxyethyl)pyridin-2-yl]ethoxy]phenyl]methyl]-1,3-thiazolidine-2,4-dione.

The dosing suspension is 15 mg Compound (1) HCl per mL and thus the new dose will be rounded to the nearest 0.1 mL.

Example 2

Evaluation of Mitochondrial pyruvate carrier (MPC) inhibitory activity of 5-[[4-[2-[5-(1-hydroxyethyl)pyridin-2-yl]ethoxy]phenyl]methyl]-1,3-thiazolidine-2,4-dione hydrochloride BRET-Assay To monitor the activity of the MPC in real time, i.e., the MPC inhibitory activity ($IC_{50}$), a BRET assay was used transfecting the appropriate chimeric proteins in HEK cells as described in Compan et al., *Molecular Cell* 59:491-501 (2015).

The MPC is a heterodimer composed of two subunits, MPC1 and MPC2. MPC1 and MPC2 interact to form an active carrier. In the assay, MPC2 was fused to Rluc8 (Donor) and MPC1 to Venus (Acceptor). These chimeric proteins were stably expressed in HEK cells. BRET activity was measured following addition of coelenterazine in the culture medium. Coelenterazine enters into cells and in contact with luciferase Rluc8 emits light, which activates the emission of fluorescence by the Acceptor, provided the distance between the Donor and Acceptor is <100 nm. If the distance between Donor and Acceptor is >100 nm, no BRET activity is measured. The level of BRET activity reflects a change in the conformation of the MPC: it is high when the carrier is in a closed conformation, low when the carrier is at rest and intermediary when it transports pyruvate. In this case, the BRET activity is the mean value between the BRET value when the carrier is at rest (Maximal distance between Donor and Acceptor) and the BRET value when it is closed (Shortest distance between Donor and Acceptor)

Figure 2:
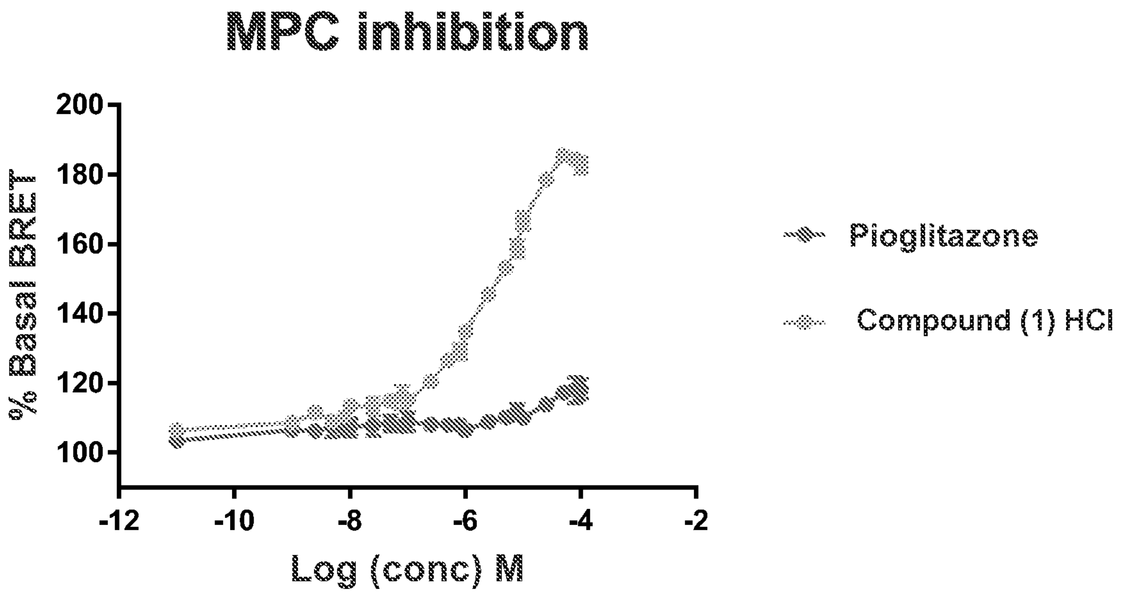
FIG. 2 is a line graph showing the comparison of the MPC inhibitory effects of Compound (1) HCl and pioglitazone in an in vitro MPC inhibitory activity model using BRET-assay in HEK cells.

A wide range of concentrations of each of the tested compounds was used from 1 nM to 100 μM. The dose response curves of the tested compounds Compound (1) HCl and pioglitazone, and are shown in FIG. 2.

The BRET activity measured for each tested compound was compared with the BRET activity obtained when HEK cells are incubated in PBS (resting state) and in PBS+ pyruvate, which corresponds to the intermediary value between the resting state and the close state (maximal closure obtained with UK5099). Table 1 below provides the $IC_{50}$ values for the tested compounds Compound (1) HCl, pioglitazone, rosiglitazone, and UK5099 obtained in the BRET assay described above.

TABLE 1

| Compound | IC50 |
|---|---|
| MIN-102 | 4.1 μM |
| Rosiglitazone | 2 μM |
| UK5099 | 17 nM |
| Pioglitazone | >100 μM |

Compound (1) HCl inhibits the MPC activity in the BRET assay with an $IC_{50}$ value of 4.1 μM. The activity of Compound (1) HCl is slightly lower than the activity of Rosiglitazone ($IC_{50}$=2 μM). Accordingly, Compound (1) HCl is a MPC inhibitor with an $IC_{50}$ of 4.1 μM, whereas pioglitazone does not inhibit MPC having an $IC_{50}$ value more than 100 μM.

Mitochondrial Respiration

To determine whether Compound (1) HCl has any effect on pyruvate-mediated mitochondrial respiration, the extracellular flux analyzer Seahorse was used as described in Compan et al., Seahorse experiments were performed in the following cell lines: HeLa (Cervix cancer cells), A549 (lung cancer cells), wild type MDA MB 231, and MDA MB 231 in which MPC2 has been deleted, leading to inactivation of the MPC (MDA MB231 KO). MDA MB231 cells are epithelial breast cancer cells. Cells were incubated with increasing concentrations of the compounds for one hour at 37° C. before oxygen consumption rate (OCR) measurements. The Seahorse analyzer allowed to measure basal and maximal respiration measured upon depolarization with 1 μM CCCP.

Figure 3A:
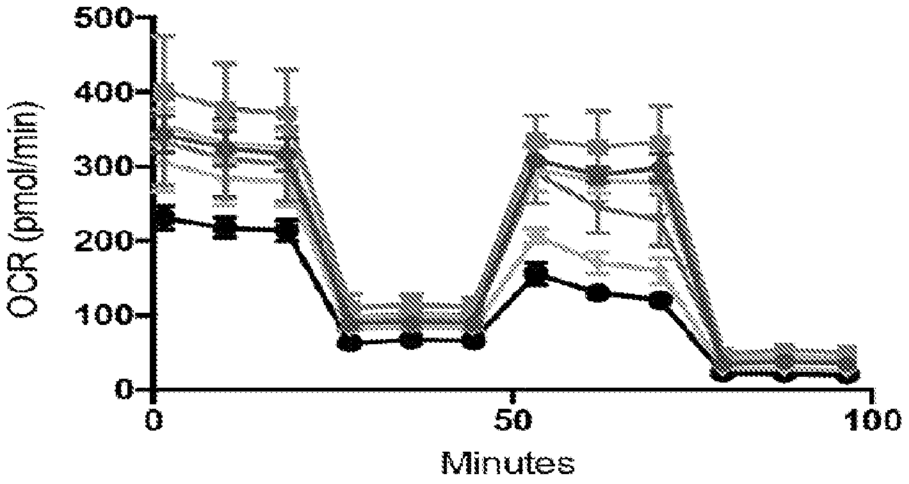
FIG. 3A is a line graph showing the effect of Compound (1) HCl on OCR in Hela cells.
Figure 3B:
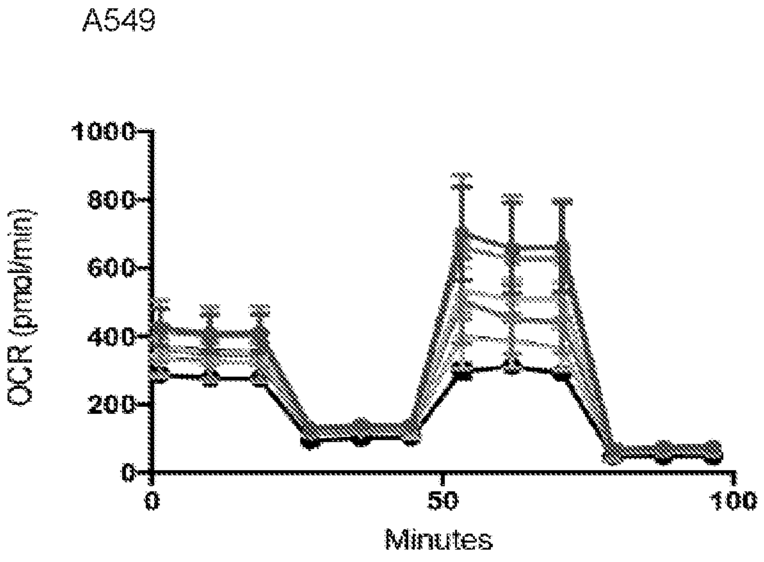
FIG. 3B is a line graph showing the effect of Compound (1) HCl on OCR in A549 cells.

Effects of Compound (1) HCl on oxygen consumption rates (OCR) in HeLa cells (FIG. 3A) and A549 cells (FIG. 3B) in a representative experiment of n=3. OCR values are expressed as ratios of OCR in the presence of different concentrations of compounds over the OCR in PBS alone. $IC_{50}$ in both cells lines was around 5 μM.

Figure 4A:
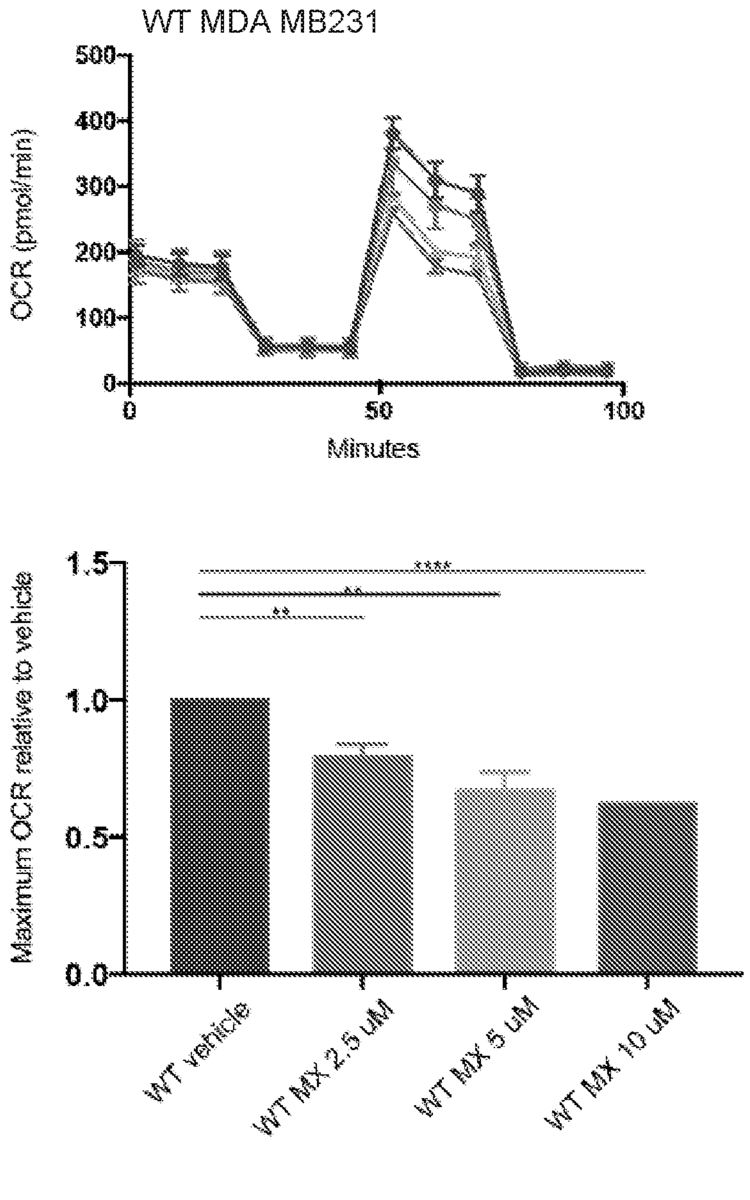
FIG. 4A is a line graph and bar graph showing the effect of Compound (1) HCl on OCR in wild type MDA MB231 cells.
Figure 4B:
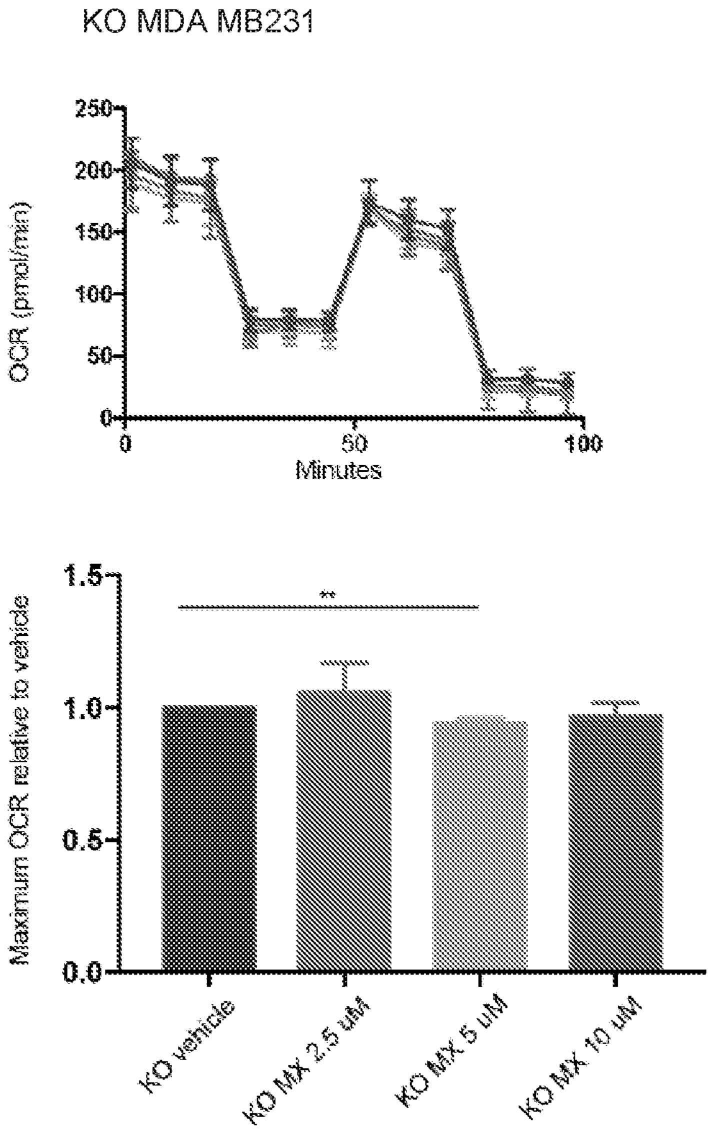
FIG. 4B is a line graph and bar graph showing the effect of Compound (1) HCl on OCR in MDA MB231 KO cells.

FIG. 4A shows the effects of Compound (1) HCl on wild type MDA MB231 cells and FIG. 4B shows the effects of Compound (1) HCl MDA MB231 KO cells. The KO cells have been deleted of the MPC2 gene and therefore they display no MPC activity. The top panel show a representative experiment of either wild type (WT) or KO cell lines. The bottom panel shows the mean values of maximal OCR in 3 different experiments. OCR values are expressed as ratios of OCR in the presence of different concentrations of the tested compound over the OCR in PBS alone.

Conclusion

Compound (1) HCl inhibits the MPC activity with an $IC_{50}$ value of 4.1 μM and inhibits oxygen consumption in a MPC dependent manner. 5 Compound (1) HCl does not inhibit oxygen consumption when the activity of the MPC has been genetically deleted, supporting that Compound (1) HCl is a specific inhibitor of MPC. The inhibitory activity of Compound (1) HCl on the MPC is low compared to the activity of UK5099 ($IC_{50}$=17 nM), a potent chemical compound inhibitor of MPC, and slightly lower than, but in the same range as, the activity of rosiglitazone ($IC_{50}$=2 μM). Compound (1) HCl is significantly more potent than pioglitazone.

Based on the results, it can be concluded that Compound (1) HCl would offer better treatment than pioglitazone for diseases in which the energetic requirements are modified.

Example 3

5-[[4-[2-[5-(1-hydroxyethyl)pyridin-2-yl]ethoxy]phenyl]methyl]-1,3-thiazolidine-2,4-dione hydrochloride significantly increases adiponectin levels in plasma Mitochondrial function is linked to adiponectin synthesis in adipocytes, and mitochondrial dysfunction in adipose tissue may explain decreased plasma adiponectin levels in obesity. Impaired mitochondrial function activates a series of mechanisms involving ER stress, JNK, and ATF3 to decrease adiponectin synthesis. See, Eun Hee Koh et al., *Diabetes* 56(12):2973-2981 (2007). In addition, hepatic adiponectin receptors are diminished in NASH patients and adiponectin knockout mice develop a more extensive liver fibrosis compared with wild-type animals, whereas adenovirus-mediated overexpression of adiponectin ameliorates liver damage in wild-type mice. (See, e.g., Kamada et al., *Gastroenterology* 125:1796-1807 (2003)).

Evaluation of effect of Compound (1) HCl on adiponectin was performed in Sprague Dawley wild type rats as a measure of PPAR gamma engagement. The rats were treated for 7 days with increasing doses of Compound (1) HCl at 54 mg/Kg/day. Plasma were obtained at 1 h after the last Compound (1) HCl administration. Adiponectin levels were measured by ELISA. Results were represented as mean+ standard error of the mean of n=8. Data were analyzed by Kruskal-Wallis followed by the Dunn post-hoc test versus the vehicle group (****, p<0.0001).

Figure 5:
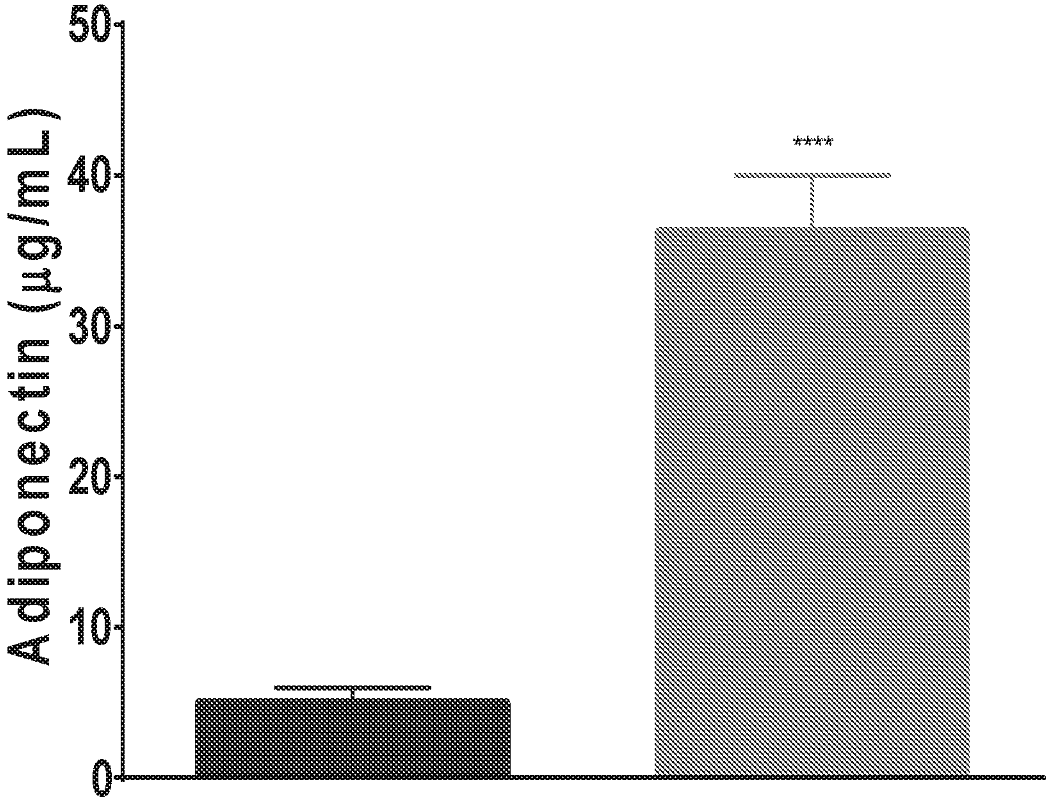
FIG. 5 represents a comparison of adiponectin levels in Sprague Dawley rats after treatment with Compound (1) HCl.

Compound (1) HCl treatment significantly increased the levels of adiponectin (FIG. 5).

Example 4

Effects of 5-[[4-[2-[5-(1-hydroxyethyl)pyridin-2-yl]ethoxy]phenyl]methyl]-1,3-thiazolidine-2,4-dione hydrochloride in the Methionine Choline Deficient Diet Fed Mice The preventive effects of Compound (1) HCl was evaluated in a 7-week Methionine Choline Deficient (MCD) diet NASH mouse model (Verdelho Machado et al.). After the acclimation period, C57BL6/J male mice (n=20) were weighed and randomized into 2 homogenous treatment groups based on body weight (n=10/group), put on a MCD diet, and treated BID orally with vehicle or Compound (1) HCl for 7 weeks.

Compound (1) HCl was dosed 62.5 mg/kg BID orally by gavage.

When C57BL6/J mice are fed a MCD diet, they rapidly develop liver steatosis, inflammation and fibrosis with concomitant increase in plasma alanine transaminase (ALT)/aspartate aminotransferase (AST) levels.

Material and Methods

After the acclimation period, C57BL6/J male mice (n=20) were weighed and randomized into 2 homogenous treatment groups based on body weight (n=10/group), put on a MCD diet, and treated BID orally with a vehicle or Compound (1) HCl (125 mg/Kg/day) for 7 weeks. Body weight was measured 3 times/week until the end of the experimental phase.

At 7 weeks of diet/treatment, mice were weighed and treated at ~08:00 am in the morning, then bled (maximal volume/EDTA) at ~1:00 pm. Plasma was then immediately isolated and stored at −80° C. prior to assay plasma ALT and AST. The plasma volume left over was stored at −80° C. for eventual additional analysis.

After blood collection, the mice were sacrificed by cervical dislocation under isoflurane anesthesia and exsanguinated with sterile saline.

A NAFLD scoring system (NAS) adapted from Kleiner et al. (Hepatology. 41(6):1313-1321 (2005)) using the criteria described in the Table 2 below:

TABLE 2

NAFLD Scoring System ("NAS")

| Score | Steatosis | Inflammation | Fibrosis | Hepatocyte ballooning |
|---|---|---|---|---|
| 0 | <5% of liver parenchyma | No foci | None | None |
| 1 | 5-to-33% of liver perenchyma | <2 foci at 20x field | Zone 3 and/or perisinusoidal fibrosis | Minimal to mild focal involving fewer than 3 hepatocytes per foci |
| 2 | 34-to-66% of liver parenchyma | 2-to-4 foci at 20x field | As grade 1 and portal fibrosis | Moderate multifocal involving more than 3 hepatocytes per foci |
| 3 | >66% of liver parenchyma | >4 foci at 20x field | As grade 2 and bridging fibrosis | Prominent multifocal involving large number of hepatocytes |
| 4 | Not applicable | Not applicable | Cirrhosis | Not applicable |

Several other histopathological observations described in clinical human cases and originally reported in the NAS scoring system published by Kleiner et al. were not observed in this animal study, such as lipogranuloma, acidophil bodies, megamitochondria, and pigmented macrophages. Therefore, it was elected not to include them in the scoring system described above. An individual mouse NAS total score was calculated for each animal by summing up the score for (1) hepatocellular steatosis, (2) liver inflammation, (3) lobular fibrosis, and (4) hepatocyte ballooning.

Results

The mice under MCD diet showed substantial body weight loss. However, the mice treated with Compound (1) HCl showed a less severe decline in body weight loss, from day 14 to day 50, leading to significant differences between day 30 and day 50.

Also, MCD diet resulted in very high ALT and AST plasma levels (mean values of 480 U/L and 455 U/L, respectively) at the end of the treatment. Compound (1) HCl substantially reduced both plasma ALT and AST levels by 78% and 55%, respectively (both p<0.01 vs. vehicle).

Also, mice treated with Compound (1) HCl did not show a change in hepatic cholesterol levels, but showed a dramatic reduction in hepatic triglycerides levels by 92% (p<0.001 vs. vehicle).

Histology analysis was performed (oil red O, H&E and Sirius Red staining) for NAFLD scoring system (NAS) for liver steatosis, inflammation, fibrosis and hepatocyte ballooning.

Mean NAS group scores were 3.40±0.3 and 0.44±01 in vehicle and Compound (1) HCl, respectively ($p<0.001$ vs. vehicle). The strong reduction in the NAS score was related to a blunted steatosis score ($p<0.001$ vs. vehicle), which was confirmed by an extremely low oil red o staining % as compared with vehicle ($p<0.001$), and a total disappearance of inflammation.

In conclusion, the present study demonstrates a reduction in liver steatosis and inflammation in MCD mice treated with Compound (1) HCl.

Having now fully described this disclosure, it will be understood by those of ordinary skill in the art that the same can be performed within a wide and equivalent range of conditions, formulations, and other parameters without affecting the scope of the invention or any embodiment thereof.

Other embodiments of the disclosure will be apparent to those skilled in the art from consideration of the specification and practice of the invention disclosed herein. It is intended that the specification and examples be considered exemplary only, with a true scope and spirit of the invention being indicated by the following claims.

All patents, patent applications, and publications cited herein are fully incorporated by reference herein in their entirety.

What is claimed is:

1. A method of administering a therapeutically effective amount of 5-[[4-[2-[5-(1-hydroxyethyl)pyridin-2-yl]ethoxy] phenyl]methyl]-1,3-thiazolidine-2,4-dione to treat a disease or disorder in a patient in need thereof, wherein the disease or disorder is chronic granulomatous disorder, a polycystic ovary syndrome, a thyroid carcinoma, a thyroid autoimmune disorder, a pituitary adenoma, atherosclerosis, a skin disease, or an inflammatory respiratory disease, the method comprising:

(a) administering an amount of 5-[[4-[2-[5-(1-hydroxyethyl)pyridin-2-yl]ethoxy]phenyl]methyl]-1,3-thiazolidine-2,4-dione, or a pharmaceutically acceptable salt thereof, to the patient per day;

(b) obtaining a plasma sample from the patient after at least four days of administering according to (a);

(c) determining the plasma concentration of 5-[[4-[2-[5-(1-hydroxyethyl)pyridin-2-yl]ethoxy]phenyl]methyl]-1,3-thiazolidine-2,4-dione in the plasma sample obtained in (b); and (d) administering a recalculated amount of 5-[[4-[2-[5-(1-hydroxyethyl)pyridin-2-yl]ethoxy]phenyl]methyl]-1,3-thiazolidine-2,4-dione, or a pharmaceutically acceptable salt thereof, in milligrams, to the patient per day as determined according to the Equation 1:

$$\text{recalculated amount in mg} = SD \times \left(\frac{CMT}{PC}\right), \quad \text{Equation 1}$$

wherein:

SD is the amount of 5-[[4-[2-[5-(1-hydroxyethyl)pyridin-2-yl]ethoxy]phenyl]methyl]-1,3-thiazolidine-2,4-dione, or a pharmaceutically acceptable salt thereof, administered to the patient in (a) in mg;

CMT is the $C_{min\ target}$ in ng/mL;

$C_{min\ target}$=(target AUC in ng h/mL×0.0341±20%)−1104±20%; and

PC is the plasma concentration in ng/mL of 5-[[4-[2-[5-(1-hydroxyethyl)pyridin-2-yl]ethoxy]phenyl]methyl]-1,3-thiazolidine-2,4-dione determined in (c), wherein the target AUC is about 100 μg h/mL to about 300 μg h/mL.

2. The method of claim 1, wherein the plasma sample is obtained from the patient after at least 7 days of administering according to (a).

3. The method of claim 1, wherein 5-[[4-[2-[5-(1-hydroxyethyl)pyridin-2-yl]ethoxy]phenyl]methyl]-1,3-thiazolidine-2,4-dione hydrochloride is administered to the patient per day in (a) and (d).

4. The method of claim 3, wherein about 180 mg of 5-[[4-[2-[5-(1-hydroxyethyl)pyridin-2-yl]ethoxy]phenyl] methyl]-1,3-thiazolidine-2,4-dione hydrochloride is administered to the patient per day in (a) and the target AUC is about 200 ng·h/mL.

5. The method of claim 3, wherein a recalculated amount of 5-[[4-[2-[5-(1-hydroxyethyl)pyridin-2-yl]ethoxy]phenyl] methyl]-1,3-thiazolidine-2,4-dione hydrochloride is administered to the patient per day in (d).

6. The method of claim 3, wherein the 5-[[4-[2-[5-(1-hydroxyethyl)pyridin-2-yl]ethoxy]phenyl]methyl]-1,3-thiazolidine-2,4-dione hydrochloride is administered to the patient in (a) and (d) as a suspension comprising about 15 mg of 5-[[4-[2-[5-(1-hydroxyethyl)pyridin-2-yl]ethoxy]phenyl]methyl]-1,3-thiazolidine-2,4-dione hydrochloride per mL.

7. A method of administering a therapeutically effective amount of 5-[[4-[2-[5-(1-hydroxyethyl)pyridin-2-yl]ethoxy] phenyl]methyl]-1,3-thiazolidine-2,4-dione to treat a disease or disorder in a patient in need thereof, wherein the disease or disorder is chronic granulomatous disorder, a polycystic ovary syndrome, a thyroid carcinoma, a thyroid autoimmune disorder, a pituitary adenoma, atherosclerosis, a skin disease, or an inflammatory respiratory disease, the method comprising:

(a) administering 5 to 20 milliliters of an oral suspension of 5-[[4-[2-[5-(1-hydroxyethyl)pyridin-2-yl]ethoxy] phenyl]methyl]-1,3-thiazolidine-2,4-dione hydrochloride to the patient per day, wherein the oral suspension comprises 15 mg of 5-[[4-[2-[5-(1-hydroxyethyl)pyridin-2-yl]ethoxy]phenyl]methyl]-1,3-thiazolidine-2,4-dione hydrochloride per mL;

(b) obtaining a plasma sample from the patient following 5 days or more of administering according to (a);

(c) determining the $C_{min\ ss}$ of 5-[[4-[2-[5-(1-hydroxyethyl)pyridin-2-yl]ethoxy]phenyl]methyl]-1,3-thiazolidine-2,4-dione in the plasma sample obtained in (b); and (d) administering a recalculated amount, in milliliters, of the oral suspension to the patient per day as determined according to the Equation 4:

$$\text{Dose}_{V1} = \text{Dose}_{pre\text{-}V1} \times \frac{C_{min_{TAR}}}{C_{min_{V1}}}, \quad \text{Equation 4}$$

wherein:

$\text{Dose}_{V1}$ is the recalculated amount, in milliliters, of the oral suspension administered to the patient per day in (d);

$\text{Dose}_{pre\text{-}V1}$ is the amount, in milliliters, of the oral suspension administered to the patient in (a);

$C_{min_{V1}}$ is the $C_{min\ ss}$, in ng/mL, of 5-[[4-[2-[5-(1-hydroxyethyl)pyridin-2-yl]ethoxy]phenyl]methyl]-1,3-thiazolidine-2,4-dione determined in (c) taken 22 hours to 26 hours after the last administration; and $C_{min_{TAR}}$ is the targeted concentration in ng/mL of 5-[[4-[2-[5-(1-hydroxyethyl)pyridin-2-yl]ethoxy]phenyl]methyl]-1,3-thiazolidine-2,4-dione, wherein:

(A) $C_{min_{TAR}}$ is calculated according to Equation 5A:

$$C_{min_{TAR}}=7700-(88.5\times Dose_{pre\text{-}V1}) \quad \text{Equation 5A}$$

if the plasma sample in (b) was obtained 18 hours to 19.9 hours after the last administration of the oral suspension in (a);

(B) $C_{min_{TAR}}$ is calculated according to Equation 5B:

$$C_{min_{TAR}}=7440-(103.4\times Dose_{pre\text{-}V1}) \quad \text{Equation 5B}$$

if the plasma sample in (b) was obtained 20 hours to 21.9 hours after the last administration of the oral suspension in (a);

(C) $C_{min_{TAR}}$ is 5716 if the plasma sample in (b) was obtained 22 hours to 25.9 hours after the last administration of the oral suspension in (a);

(D) $C_{min_{TAR}}$ is calculated according to Equation 5D:

$$C_{min_{TAR}}=6740-(138.6\times Dose_{pre\text{-}V1}) \quad \text{Equation 5D}$$

if the plasma sample in (b) was obtained 26 hours to 27.9 hours after the last administration of the oral suspension in (a); or (E) $C_{min_{TAR}}$ is calculated according to Equation 5E:

$$C_{min_{TAR}}=6520-(148.0\times Dose_{pre\text{-}V1}) \quad \text{Equation 5E}$$

if the plasma sample in (b) was obtained 28 hours to 30 hours after the last administration of the oral suspension in (a).

8. The method of claim 7 further comprising:

(i) obtaining a plasma sample from the patient following 5 days or more of administering the recalculated amount, in milliliters, of the oral suspension of 5-[[4-[2-[5-(1-hydroxyethyl)pyridin-2-yl]ethoxy]phenyl]methyl]-1,3-thiazolidine-2,4-dione hydrochloride to the patient per day in (d);

(ii) determining the $C_{min_{calcd}}$, in ng/mL, of 5-[[4-[2-[5-(1-hydroxyethyl)pyridin-2-yl]ethoxy]phenyl]methyl]-1,3-thiazolidine-2,4-dione in the plasma sample obtained in (i) according to Equation 6:

$$C_{min_{calcd}} = \frac{Dose_{V1} \times C_{min_{V2}}}{Dose_{last\ taken}}; \quad \text{Equation 6}$$

wherein $Dose_{last\ taken}$ is the amount, in milliliters, of the last administered dose of the oral suspension taken by the patient;

(iii) determining the $AUC_{Calcd}$, in μg·h/mL, of 5-[[4-[2-[5-(1-hydroxyethyl)pyridin-2-yl]ethoxy]phenyl]methyl]-1,3-thiazolidine-2,4-dione based on the $C_{min_{Calcd}}$ determined in (ii), wherein:

(A) the $AUC_{Calcd}$ is calculated according to Equation 7A:

$$AUC_{Calcd} = \frac{C_{min_{calcd}} + (88.5 \times Dose_{last\ taken})}{38.5}, \quad \text{Equation 7A}$$

if the plasma sample in (i) was obtained between 18 hours to 19.9 hours after the last administration of the oral suspension;

(B) the $AUC_{Calcd}$ is calculated according to Equation 7B:

$$AUC_{Calcd} = \frac{C_{min_{calcd}} + (103.4 \times Dose_{last\ taken})}{37.2}, \quad \text{Equation 7B}$$

if the plasma sample in (i) was obtained 20 hours to 21.9 hours after the last administration of the oral suspension;

(C) the $AUC_{Calcd}$ is calculated according to Equation 7C:

$$AUC_{Calcd} = \frac{C_{min_{calcd}} + 1104.1}{34.1}, \quad \text{Equation 7C}$$

if the plasma sample in (i) was obtained 22 hours to 25.9 hours after the last administration of the oral suspension;

(D) the $AUC_{Calcd}$ is calculated according to Equation 7D:

$$AUC_{Calcd} = \frac{C_{min_{calcd}} + (138.6 \times Dose_{last\ taken})}{33.7}, \quad \text{Equation 7D}$$

if the plasma sample in (i) was obtained 26 hours to 27.9 hours after the last administration of the oral suspension; or (E) the $AUC_{Calcd}$ is calculated according to Equation 7E:

$$AUC_{Calcd} = \frac{C_{min_{calcd}} + (148 \times Dose_{last\ taken})}{32.6}, \quad \text{Equation 7E}$$

if the plasma sample in (i) was obtained 28 hours to 30 hours after the last administration of the oral suspension; and (iv) administering the same recalculated amount, in milliliters, of the oral suspension to the patient per day as in (i) for 5 days or more if the $AUC_{Calcd}$ is 150 to 240 μg h/mL and, optionally, repeating (i)-(iii); or (v) administering a new recalculated amount, in milliliters, of the oral suspension to the patient per day in (i) if the $AUC_{Calcd}$ is less than 150 or more than 240 μg h/mL.

9. A method of administering a therapeutically effective amount of 5-[[4-[2-[5-(1-hydroxyethyl)pyridin-2-yl]ethoxy]phenyl]methyl]-1,3-thiazolidine-2,4-dione to treat a disease or disorder in a patient in need thereof, wherein the disease or disorder is chronic granulomatous disorder, a polycystic ovary syndrome, a thyroid carcinoma, a thyroid autoimmune disorder, a pituitary adenoma, atherosclerosis, a skin disease, or an inflammatory respiratory disease, the method comprising:

(a) administering an initial dose of 5-[[4-[2-[5-(1-hydroxyethyl)pyridin-2-yl]ethoxy]phenyl]methyl]-1,3-thiazolidine-2,4-dione hydrochloride to the patient once per day for 5 or more days; and (b) administering a recalculated dose of 5-[[4-[2-[5-(1-hydroxyethyl)pyridin-2-yl]ethoxy]phenyl]methyl]-1,3-thiazolidine-2,4-dione hydrochloride according to:

(i) Equation 8a:

$$D_{recal}=D_{initial}*(AUC_{Tar}/AUC\_0t) \quad \text{Equation 8a}$$

wherein:

$D_{recal}$ is recalculated dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

$D_{initial}$ is the initial dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

$AUC_{Tar}$ is the targeted exposure of 5-[[4-[2-[5-(1-hydroxyethyl)pyridin-2-yl]ethoxy]phenyl]methyl]-1,3-thiazolidine-2,4-dione in the patient 24 hours after the last administration in (a) in ng h/ml; and AUC_0t is the calculated exposure of 5-[[4-[2-[5-(1-hydroxyethyl)pyridin-2-yl]ethoxy]phenyl]methyl]-1,3-thiazolidine-2,4-dione in the patient 24 hours after the last administration in (a) in ng h/ml; and (ii) Equation 8b:

$$AUC\_0t=(28.31+0.472*\Delta T)*C+(34410+2234*\Delta T)*D_{initial}/150 \quad \text{Equation 8b}$$

wherein:

AUC_0t is the calculated exposure of 5-[[4-[2-[5-(1-hydroxyethyl)pyridin-2-yl]ethoxy]phenyl]methyl]-1,3-thiazolidine-2,4-dione in the patient 24 hours after the last administration in (a) in ng h/ml;

$D_{initial}$ is the initial dose of the 5-[[4-[2-[5-(1-hydroxyethyl)pyridin-2-yl]ethoxy]phenyl]methyl]-1,3-thiazolidine-2,4-dione hydrochloride administered to the patient in milligrams;

C is the plasma concentration of 5-[[4-[2-[5-(1-hydroxyethyl)pyridin-2-yl]ethoxy]phenyl]methyl]-1,3-thiazolidine-2,4-dione in the patient in ng/ml, wherein the plasma sample is taken from the patient 24±6 hours after the last administration in (a); and ΔT is the difference between the time the plasma sample is taken from the patient and 24 hours after the last administration in (a) in hours;

wherein the targeted exposure is 50,000 ng h/mL to 250,000 ng h/mL.

10. The method of claim 9, the targeted exposure is 100,000 ng·h/mL to 200,000 ng·h/mL.

11. The method of claim 9, the targeted exposure is 50,000 ng·h/mL to 100,000 ng·h/mL.

12. The use of claim 1, wherein the target AUC is about 50 μgh/mL to about 100 μgh/mL.

* * * * *